(12) United States Patent
Kataoka et al.

(10) Patent No.: US 9,102,630 B2
(45) Date of Patent: Aug. 11, 2015

(54) CRYSTALS OF SALTS OF PHENYLALANINE DERIVATIVES

(71) Applicant: AJINOMOTO CO., INC., Chuo-ku (JP)

(72) Inventors: Noriyasu Kataoka, Ota-ku (JP); Riho Kodama, Kawasaki (JP); Akinori Tatara, Yokohama (JP)

(73) Assignee: AJINOMOTO CO., INC., Chuo-ku (JP)

( * ) Notice: Subject to any disclaimer, the term of this patent is extended or adjusted under 35 U.S.C. 154(b) by 0 days.

(21) Appl. No.: 14/206,540

(22) Filed: Mar. 12, 2014

(65) Prior Publication Data

US 2014/0206705 A1 Jul. 24, 2014

Related U.S. Application Data

(63) Continuation of application No. 13/632,474, filed on Oct. 1, 2012, which is a continuation of application No. PCT/JP2011/057798, filed on Mar. 29, 2011.

(30) Foreign Application Priority Data

Mar. 29, 2010 (JP) ................................ 2010-074617

(51) Int. Cl.
  *A61K 31/517* (2006.01)
  *C07D 239/72* (2006.01)
  *C07D 239/96* (2006.01)

(52) U.S. Cl.
  CPC .................................... *C07D 239/96* (2013.01)

(58) Field of Classification Search
  CPC ............................ A61K 31/517; C07D 239/72
  USPC ........ 544/242, 253, 286; 514/247, 256, 258.1
  See application file for complete search history.

(56) References Cited

U.S. PATENT DOCUMENTS

| | | |
|---|---|---|
| 7,345,049 B2 | 3/2008 | Sagi et al. |
| 7,683,169 B2 * | 3/2010 | Takahashi et al. ............ 544/283 |
| 7,737,274 B2 | 6/2010 | Kataoka et al. |
| 7,842,700 B2 | 11/2010 | Fujita et al. |
| 7,872,125 B2 * | 1/2011 | Makino et al. ................ 544/284 |
| 7,951,942 B2 * | 5/2011 | Takahashi et al. ............ 544/283 |
| 8,058,432 B2 | 11/2011 | Kataoka et al. |
| 8,268,844 B2 | 9/2012 | Fujita et al. |
| 8,309,561 B2 | 11/2012 | Sagi et al. |
| 8,318,975 B2 | 11/2012 | Kataoka et al. |
| 8,426,588 B2 | 4/2013 | Makino et al. |
| 8,518,441 B2 | 8/2013 | Higuchi et al. |
| 8,546,610 B2 | 10/2013 | Kataoka et al. |
| 2003/0220268 A1 | 11/2003 | Makino et al. |
| 2006/0009476 A1 | 1/2006 | Kataoka et al. |
| 2006/0204572 A1 | 9/2006 | Higuchi et al. |
| 2006/0204574 A1 | 9/2006 | Ogawa et al. |
| 2006/0223836 A1 | 10/2006 | Makino et al. |
| 2007/0018172 A1 | 1/2007 | Takahashi et al. |
| 2010/0137593 A1 | 6/2010 | Takahashi et al. |
| 2010/0204505 A1 | 8/2010 | Kataoka et al. |
| 2011/0065918 A1 | 3/2011 | Makino et al. |
| 2012/0253041 A1 | 10/2012 | Makino et al. |
| 2013/0030013 A1 | 1/2013 | Aburatani et al. |

FOREIGN PATENT DOCUMENTS

| | | |
|---|---|---|
| EP | 1 288 205 A1 | 3/2003 |
| EP | 1 595 870 A1 | 11/2005 |
| EP | 1 683 524 A1 | 7/2006 |
| EP | 1 688 410 A1 | 8/2006 |
| WO | WO 02/16329 | 2/2002 |
| WO | WO 2004/074264 | 9/2004 |
| WO | WO 2005/046696 | 5/2005 |
| WO | WO 2005/051925 | 6/2005 |
| WO | WO 2006/137450 A1 | 12/2006 |

OTHER PUBLICATIONS

P. Heinrich Stahl, et al., "Handbook of Pharmaceutical Salts", Wiley-VCH, 2002, pp. 1-7, 288-290, 294, 295, 298, 306, 309-310.
C. Wermuth, "The Practice of Medicinal Chemistry", Saishin Soyaku Kagak, last volume, Sep. 25, 1999, pp. 347-354.
C. Wermuth, "The Practice of Medicinal Chemistry", Academic Press, 1996, pp. 739-746. (*Original English Edition of reference AX*).
Japanese Office Action issued Jan. 21, 2015 in Patent Application No. 2012-508341 (with English Translation).
Extended European Search Report issued Apr. 24, 2014 in Patent Application No. 11762843.8.

(Continued)

*Primary Examiner* — Golam M M Shameem
(74) *Attorney, Agent, or Firm* — Oblon, McClelland, Maier & Neustadt, L.L.P.

(57) ABSTRACT

Provided is a crystal of a salt of the compound represented by formula (I), which is excellent in its solubility in water. In particular, also provided is a crystal of hydrochloride, hydrobromate, sulfate, nitrate, p-toluenesulfonate or methanesulfonate of the compound represented by formula (I).

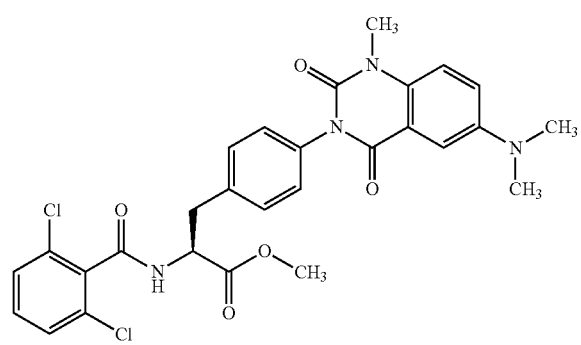

(I)

10 Claims, 28 Drawing Sheets

(56) References Cited

OTHER PUBLICATIONS

Extended European Search Report issued Mar. 2, 2015 in Patent Application No. 14197204.2.

John K. Haleblian, "Characterization of Habits and Crystalline Modification of Solids and Their Pharmaceutical Applications" Journal of Pharmaceutical Sciences, vol. 64, No. 8, XP009058363, Aug. 1975, pp. 1269-1288.

Stephen M. Berge, et al., "Pharmaceutical Salts" Journal of Pharmaceutical Sciences, vol. 66, No. 1, XP002675560, Jan. 1977, pp. 1-19.

H. P. Jones, et al., "Crystallization of a Salt of a Weak Organic Acid and Base: Solubility Relations, Supersaturation Control and Polymorphic Behavior" Journal of Physical Chemistry, vol. 109, No. 11, XP002723084, 2005, pp. 5273-5278.

Julius F. Remenar, et al., "Salt Selection and Simultaneous Polymorphism Assessment via High-Throughput Crystallization: The Case of Sertraline" Organic Process Research & Development, vol. 7, No. 6, XP002723085, 2003, pp. 990-996.

\* cited by examiner

CRYSTALS OF SALTS OF PHENYLALANINE DERIVATIVES

This application is a Continuation of U.S. application Ser. No. 13/632,474, filed on Oct. 1, 2012, which is a Continuation of PCT/JP2011/057798, filed on Mar. 29, 2011.

TECHNICAL FIELD

The present invention relates to crystals of salts of a phenylalanine derivative having a specific structure, a method for the preparation of the same and the use thereof as a medicine.

BACKGROUND ART

The compound represented by the chemical formula (I) as will be specified later (hereunder referred to as "the compound (I)") or a pharmaceutically acceptable salt thereof shows an α 4-integrin-inhibitory action in vivo, it is a compound useful as a therapeutic agent for treating, for instance, inflammatory intestinal diseases and it can be produced according to the methods disclosed in Patent Documents 1 and 2 as will be specified below. In addition, there is reported, in Patent Document 3, an form a crystal or the like of the compound (I) as a form which is excellent in the storage stability and moisture-proofing characteristics. Moreover, Patent Document 4 reports that the solubility of the compound (I) can be improved by forming the compound (I), as a drug hardly soluble in water, into a solid dispersion, while it is maintained in its amorphous state.

On the other hand, it has also been known that if such a compound forms a salt, it may be, for instance, improved in its solubility and its bioavailability, as well as the modification of characteristics of the original compound or agent (see Non-Patent Document 1 specified below). However, there has not yet been reported any crystal of a pharmaceutically acceptable salt of the compound (I) and accordingly, there has been desired for the development of a crystalline salt of the compound (I) having excellent solubility in water, while maintaining the stability thereof sufficient for use in the production of a pharmaceutical preparations containing the same.

PRIOR ART LITERATURE

Patent Document

Patent Document 1: Pamphlet of International Laid-Open Patent No. 02/16329;
Patent Document 2: Pamphlet of International Laid-Open Patent No. 2004/074264;
Patent Document 3: Pamphlet of International Laid-Open Patent No. 2005/051925;
Patent Document 4: Pamphlet of International Laid-Open Patent No. 2005/046696.

Non-Patent Document

Non-Patent Document 1: P. Heirich Stahl, Camille G. Wermuth (Eds.), "Handbook of Pharmaceutical Salts", Wiley-VCH.

DISCLOSURE OF THE INVENTION

Problems that the Invention is to Solve

It is an object of the present invention to provide a crystal of a salt of the compound (I), which is excellent in its solubility in water.

Means for the Solution of the Problems

The inventors of this invention have conducted various studies to solve the foregoing problems associated with the conventional techniques, have found that a salt of the compound (I) with an acid can form crystals having various crystalline forms when treating the same under specific conditions and that the foregoing problems can be solved through the use of such a crystal and have thus completed the present invention.

The details of the present invention will be given below:
(1) A crystal of a pharmaceutically acceptable acid-addition salt of the compound represented by the following chemical formula (I):

[Chemical Formula 1]

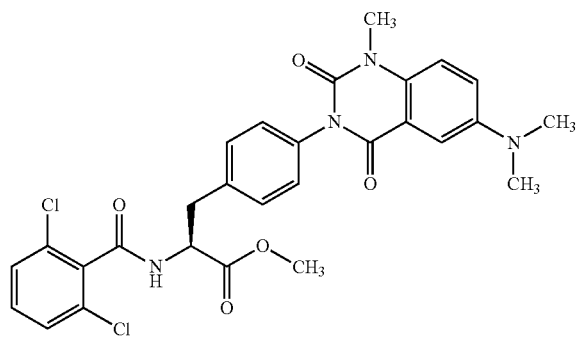

(2) The crystal as set forth in the foregoing item (1), wherein it is hydrochloride of the compound represented by the chemical formula (I).
(3) The crystal as set forth in the foregoing item (2), wherein it is form Cl 1 crystal characterized by the peaks appearing at angles (2 θ) of diffraction of 20.8, 23.6, 25.3 and 26.9 in the powder X-ray diffraction pattern.
(4) The crystal as set forth in the foregoing item (2), wherein it is form Cl 2 crystal characterized by the peaks appearing at angles (2 θ) of diffraction of 5.24, 10.39, 21.04 and 21.41 in the powder X-ray diffraction pattern.
(5) The crystal as set forth in the foregoing item (2), wherein it is form Cl 3 crystal characterized by the peaks appearing at angles (2 θ) of diffraction of 4.21, 10.13, 10.30 and 16.17 in the powder X-ray diffraction pattern.
(6) The crystal as set forth in the foregoing item (2), wherein it is form Cl 4 crystal characterized by the peaks appearing at angles (2 θ) of diffraction of 4.07, 17.84, 23.83 and 24.87 in the powder X-ray diffraction pattern.
(7) The crystal as set forth in the foregoing item (2), wherein it is form Cl 5 crystal characterized by the peaks appearing at angles (2 θ) of diffraction of 4.09, 22.12, 23.17 and 27.76 in the powder X-ray diffraction pattern.
(8) The crystal as set forth in the foregoing item (2), wherein it is form Cl 6 crystal characterized by the peaks appearing at angles (2 θ) of diffraction of 22.32, 22.90, 26.43 and 26.77 in the powder X-ray diffraction pattern.
(9) The crystal as set forth in the foregoing item (2), wherein it is form Cl 7 crystal characterized by the peaks appearing at angles (2 θ) of diffraction of 16.65, 20.99, 22.61 and 24.70 in the powder X-ray diffraction pattern.
(10) The crystal as set forth in the foregoing item (1), wherein it is hydrobromide of the compound represented by the chemical formula (I).

(11) The crystal as set forth in the foregoing item (10), wherein it is form Br1 crystal characterized by the peaks appearing at angles (2 θ) of diffraction of 14.3, 17.4, 20.5 and 24.9 in the powder X-ray diffraction pattern.

(12) The crystal as set forth in the foregoing item (10), wherein it is form Br2 crystal characterized by the peaks appearing at angles (2 θ) of diffraction of 18.9, 20.6, 23.3, 25.0 and 26.7 in the powder X-ray diffraction pattern.

(13) The crystal as set forth in the foregoing item (10), wherein it is form Br3 crystal characterized by the peaks appearing at angles (2 θ) of diffraction of 21.53, 22.12, 23.69 and 25.39 in the powder X-ray diffraction pattern.

(14) The crystal as set forth in the foregoing item (10), wherein it is form Br4 crystal characterized by the peaks appearing at angles (2 θ) of diffraction of 4.07, 17.78, 23.62 and 24.65 in the powder X-ray diffraction pattern.

(15) The crystal as set forth in the foregoing item (10), wherein it is form Br5 crystal characterized by the peaks appearing at angles (2 θ) of diffraction of 21.20, 21.98, 23.21 and 23.93 in the powder X-ray diffraction pattern.

(16) The crystal as set forth in the foregoing item (10), wherein it is form Br6 crystal characterized by the peaks appearing at angles (2 θ) of diffraction of 17.25, 23.38, 24.55 and 26.73 in the powder X-ray diffraction pattern.

(17) The crystal as set forth in the foregoing item (1), wherein it is sulfate of the compound represented by the chemical formula (I).

(18) The crystal as set forth in the foregoing item (17), wherein it is form S1 crystal characterized by the peaks appearing at angles (2 θ) of diffraction of 18.2, 22.7, 24.8 and 25.5 in the powder X-ray diffraction pattern.

(19) The crystal as set forth in the foregoing item (17), wherein it is form S2 crystal characterized by the peaks appearing at angles (2 θ) of diffraction of 15.6, 16.2, 18.0 and 19.2 in the powder X-ray diffraction pattern.

(20) The crystal as set forth in the foregoing item (17), wherein it is form S3 crystal characterized by the peaks appearing at angles (2 θ) of diffraction of 13.0, 18.7, 22.1 and 22.5 in the powder X-ray diffraction pattern.

(21) The crystal as set forth in the foregoing item (17), wherein it is form S4 crystal characterized by the peaks appearing at angles (2 θ) of diffraction of 12.58, 21.08, 23.02 and 23.93 in the powder X-ray diffraction pattern.

(22) The crystal as set forth in the foregoing item (17), wherein it is form S5 crystal characterized by the peaks appearing at angles (2 θ) of diffraction of 4.04, 21.06, 21.46 and 25.75 in the powder X-ray diffraction pattern.

(23) The crystal as set forth in the foregoing item (1), wherein it is nitrate of the compound represented by the chemical formula (I).

(24) The crystal as set forth in the foregoing item (23), wherein it is form N1 crystal characterized by the peaks appearing at angles (2 θ) of diffraction of 12.8, 22.5, 23.3 and 24.6 in the powder X-ray diffraction pattern.

(25) The crystal as set forth in the foregoing item (23), wherein it is form N2 crystal characterized by the peaks appearing at angles (2 θ) of diffraction of 18.9, 20.7, 23.5 and 26.5 in the powder X-ray diffraction pattern.

(26) The crystal as set forth in the foregoing item (1), wherein it is p-toluene-sulfonate of the compound represented by the chemical formula (I).

(27) The crystal as set forth in the foregoing item (26), wherein it is form Ts1 crystal characterized by the peaks appearing at angles (2 θ) of diffraction of 12.9, 21.5 and 23.1 in the powder X-ray diffraction pattern.

(28) The crystal as set forth in the foregoing item (1), wherein it is methane-sulfonate of the compound represented by the chemical formula (I).

(29) The crystal as set forth in the foregoing item (28), wherein it is form Ms1 crystal characterized by the peaks appearing at angles (2 θ) of diffraction of 10.1, 11.5, 21.2 and 21.9 in the powder X-ray diffraction pattern.

(30) The crystal as set forth in the foregoing item (28), wherein it is form Ms2 crystal characterized by the peaks appearing at angles (2 θ) of diffraction of 12.9, 15.9, 18.8 and 23.0 in the powder X-ray diffraction pattern.

(31) The crystal as set forth in the foregoing item (28), wherein it is form Ms3 crystal characterized by the peaks appearing at angles (2 θ) of diffraction of 11.2, 12.6, 22.9 and 25.5 in the powder X-ray diffraction pattern.

(32) The crystal as set forth in the foregoing item (28), wherein it is form Ms4 crystal characterized by the peaks appearing at angles (2 θ) of diffraction of 17.99, 19.22, 19.75 and 25.64 in the powder X-ray diffraction pattern.

(33) A pharmaceutical composition comprising a crystal as set forth in any one of the foregoing items.

(34) An α 4-integrin-inhibitor comprising a crystal as set forth in any one of the foregoing items.

(35) A therapeutic agent or a prophylactic agent for treating or preventing an inflammatory disease, wherein the α 4-integrin-dependent adhesion process is involved in the pathema, comprising a crystal as set forth in any one of the foregoing items.

(36) A therapeutic agent or a prophylactic agent for treating or preventing rheumatoid arthritis, inflammatory intestinal diseases, systemic lupus erythematosus, disseminated or multiple sclerosis, Sjogren's syndrome, asthma, psoriasis, allergy, diabetes (mellitus), cardiovascular diseases, arterial sclerosis, restenosis, tumor hyperplasia, tumor metastasis, graft rejection, characterized in that it comprises a crystal as set forth in any one of the foregoing items.

Effect of the Invention

The crystal according to the present invention can easily be handled as an original drug for preparing a pharmaceutical agent and is excellent in, in particular, solubility since it is in a crystalline form. Moreover, it preferably possesses a high stability in water sufficient for use as an original drug of a pharmaceutical preparation. Accordingly, the crystal according to the present invention can be regarded as an original drug for use in the preparation of a pharmaceutical agent or a pharmaceutical preparation, which is excellent in the absorbability or bioavailability and the ability thereof to be easily formed into a preparation.

MODE FOR CARRYING OUT THE INVENTION

Figure 1:
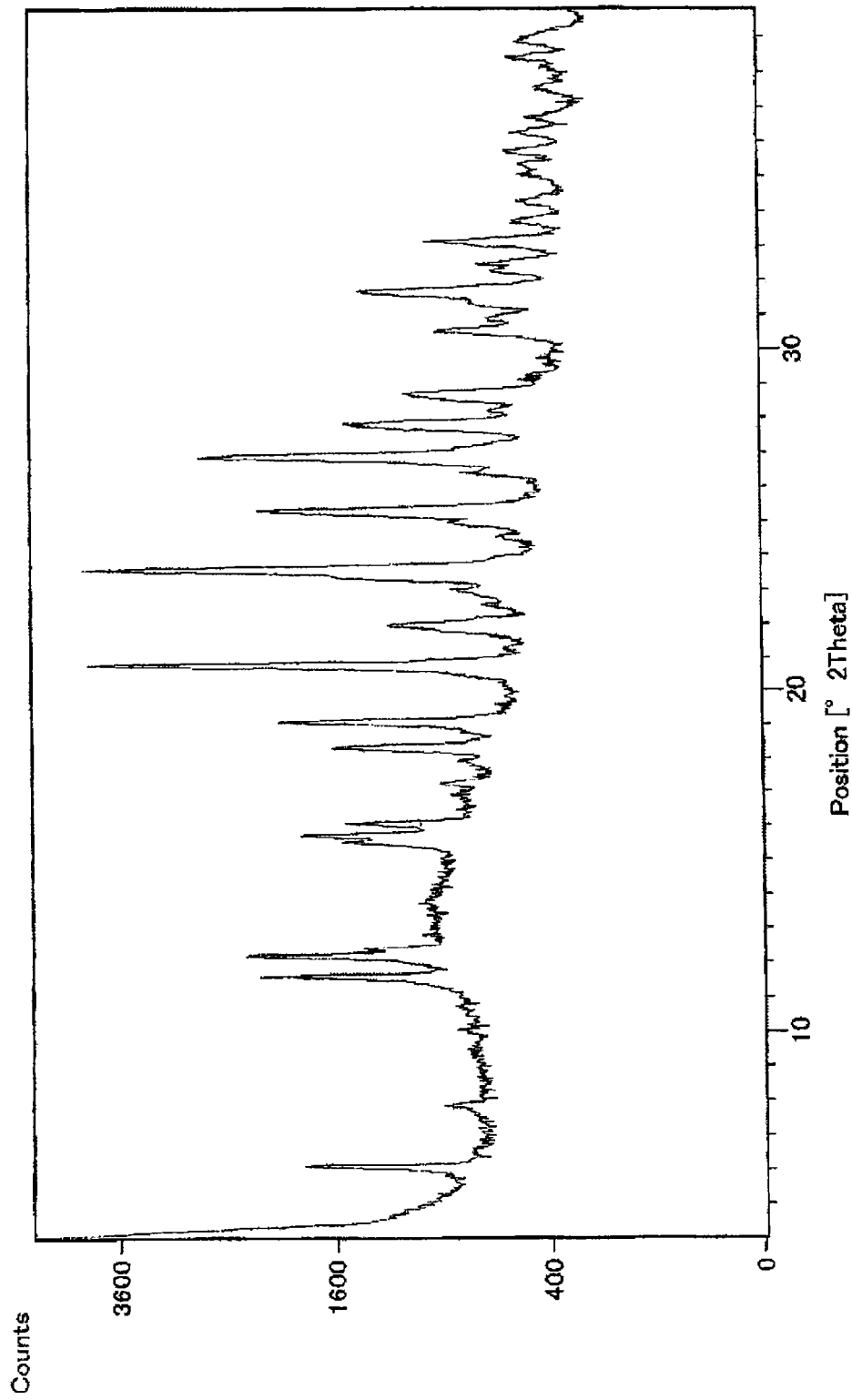
FIG. 1 is a diagram showing the powder X-ray diffraction pattern observed for the form Cl 1 crystal according to the present invention wherein the angle of diffraction: 2 θ (degrees) is plotted as abscissa, while the intensity (counts) is plotted as ordinate.

The compound represented by the foregoing chemical formula (I) is disclosed in Example 196 of Patent Document 1 and Example 1 of Patent Document 2 and accordingly, it can be prepared according to the disclosure of these prior art documents.

Regarding the pharmaceutically acceptable acid-addition salts of the compound represented by the chemical formula (I), the pharmaceutically acceptable acid is not restricted to any particular one inasmuch as it can form a salt with the compound (I). Preferred examples thereof include hydrochloric acid, hydrobromic acid, sulfuric acid, nitric acid, p-toluene-sulfonic acid, and methane-sulfonic acid. In this respect, particularly preferably used herein as such acids are hydrochloric acid and hydrobromic acid, among others.

The crystals of hydrochloride of the compound (I) may be those of the hydrochloride in the form of hydrates and solvates thereof and, more specifically, examples thereof include form Cl 1 crystals, form Cl 2 crystals, form Cl 3 crystals, form Cl 4 crystals, form Cl 5 crystals, form Cl 6 crystals and form Cl 2 crystals.

The form Cl 1 crystal is a crystal of hydrochloride of the compound (I), it shows the peaks at angles (2 θ) of diffraction of 20.8, 23.6, 25.3 and 26.9 and more preferably the peaks at angles of diffraction of 6.1, 11.6, 12.2, 15.7, 19.1, 20.8, 23.6, 25.3, 26.9, 27.8 and 31.7, in the powder X-ray diffraction pattern. The form Cl 1 crystal can preferably be prepared by blending a mixture comprising methanol, the compound (I) and hydrogen chloride preferably with ethanol, isopropyl alcohol or mixture thereof and then recovering the resulting crystals. Alternatively, hydrochloride of the compound (I) is prepared in advance, the resulting hydrochloride of the compound is then blended with methanol to give a mixture and subsequently the same procedures used above are repeated except for using the resulting mixture to thus give desired form Cl 1 crystals of the compound (I). In this respect, the form Cl 1 crystal can likewise be obtained by drying the form Cl 2 crystal under reduced pressure and then adjusting the moisture content of the vacuum dried-product.

The form Cl 2 crystal is a crystal of hydrochloride of the compound (I) and it shows the peaks appearing at angles (2 θ) of diffraction of 5.24, 10.39, 21.04 and 21.41 and more preferably the peaks appearing at angles of diffraction of 5.24, 10.39, 11.10, 15.56, 21.04, 21.41, 24.82, 25.36, 25.97 and 28.82, in the powder X-ray diffraction pattern. The form Cl 2 crystal can preferably be prepared by blending a mixture comprising methanol, the compound (I) and hydrogen chloride preferably with ethanol and then recovering the crystals precipitated out of the mixture. Alternatively, hydrochloride of the compound (I) is prepared in advance, the resulting hydrochloride is then blended with ethanol to give a mixture and subsequently the same procedures used above are repeated except for using the resulting mixture to thus give desired form Cl 2 crystals of the compound (I).

The form Cl 3 crystal is a crystal of hydrochloride of the compound (I) and it shows the peaks appearing at angles (2 θ) of diffraction of 4.21, 10.13, 10.30 and 16.17 and more preferably the peaks appearing at angles of diffraction of 4.21, 10.13, 10.30, 13.15, 15.61, 16.17, 16.62, 19.49, 22.65, 23.90 and 25.80, in the powder X-ray diffraction pattern. The form Cl 3 crystal can preferably be prepared by blending a mixture comprising methanol, the compound (I) and hydrogen chloride preferably with acetone and then recovering the resulting crystals. Alternatively, hydrochloride of the compound (I) is prepared in advance, the resulting hydrochloride is then blended with acetone to give a mixture and subsequently the same procedures used above are repeated except for using the mixture prepared above to thus give desired form Cl 3 crystals of the compound (I).

The form Cl 4 crystal is a crystal of hydrochloride of the compound (I) and it shows the peaks appearing at angles (2 θ) of diffraction of 4.07, 17.84, 23.83 and 24.87 and more preferably the peaks appearing at angles of diffraction of 4.07, 10.99, 17.84, 20.94, 21.27, 22.14, 22.80, 23.83, 24.87, 27.39 and 29.86, in the powder X-ray diffraction pattern. The form Cl 4 crystal can be produced by preparing hydrochloride of the compound (I) in advance, blending the resulting hydrochloride with acetonitrile and more preferably with dichloromethane and acetonitrile to give a mixture and subsequently repeating the same procedures used above except for using the resulting mixture to thus give desired form Cl 4 crystals of the compound (I).

The form Cl 5 crystal is a crystal of hydrochloride of the compound (I) and it shows the peaks appearing at angles (2 θ) of diffraction of 4.09, 22.12, 23.17 and 27.76 and more preferably the peaks appearing at angles of diffraction of 4.09, 9.03, 12.43, 14.66, 20.86, 22.12, 23.17, 26.06, 26.45, 27.76 and 31.98, in the powder X-ray diffraction pattern. The form Cl 5 crystal can preferably be prepared by blending a mixture comprising methanol, the compound (I) and hydrogen chloride preferably with methyl acetate and then recovering the resulting crystals. Alternatively, hydrochloride of the compound (I) is prepared in advance, the resulting hydrochloride is then blended with dichloromethane and more preferably methyl acetate to give a mixture and subsequently the same procedures used above are repeated except for using the resulting mixture to thus give desired form Cl 5 crystals of the compound (I).

The form Cl 6 crystal is a crystal of hydrochloride of the compound (I) and it shows the peaks appearing at angles (2 θ) of diffraction of 22.32, 22.90, 26.43 and 26.77 and more preferably the peaks appearing at angles of diffraction of 12.64, 17.69, 20.21, 22.32, 22.90, 23.82, 25.44, 26.43, 26.77 and 29.74, in the powder X-ray diffraction pattern. The form Cl 6 crystal can be produced by preparing hydrochloride of the compound (I) in advance, blending the resulting hydrochloride with a mixed solvent comprising methyl acetate and acetonitrile to give a mixture and subsequently repeating the same procedures used above except for using the resulting mixture to thus give desired form Cl 6 crystals of the compound (I).

The form Cl 7 crystal is a crystal of hydrochloride of the compound (I) and it shows the peaks appearing at angles (2 θ) of diffraction of 16.65, 20.99, 22.61 and 24.70 and more preferably the peaks appearing at angles of diffraction of 12.34, 13.23, 15.42, 16.65, 17.48, 20.99, 22.61, 24.70, 27.27 and 27.99, in the powder X-ray diffraction pattern. The form Cl 7 crystal can be produced by preparing hydrochloride of the compound (I) in advance, blending the resulting hydrochloride with a mixed solvent comprising isopropyl alcohol, methyl acetate and tetrahydrofuran to give a mixture and subsequently repeating the same procedures used above except for using the resulting mixture to thus give desired form Cl 7 crystals of the compound (I).

The crystals of hydrobromide of the compound (I) may be those of the hydrobromide in the form of hydrates and solvates thereof and, more specifically, examples thereof include form Br1 crystals, form Br2 crystals, form Br3 crystals, form Br4 crystals, form Br5 crystals and form Br6 crystals.

The form Br1 crystal is a crystal of hydrobromide of the compound (I) and it shows the peaks appearing at angles (2 θ) of diffraction of 14.3, 17.4, 20.5 and 24.9 and more preferably the peaks appearing at angles (2 θ) of diffraction of 14.3, 15.4, 17.4, 20.5, 22.7, 23.6, 24.9 and 25.9, in the powder X-ray diffraction pattern. The form Br1 crystal can preferably be prepared by allowing, to stand, a mixture of methanol, the compound (I) and preferably acetyl bromide, preferably at room temperature and then recovering the crystals thus precipitated out of the mixture. Alternatively, it is also possible to form a desired form Br1 crystal by preparing hydrobromide of the compound (I) in advance, blending the resulting hydrobromide with methanol to give a mixture and then repeating the same procedures used above except for using the mixture thus obtained.

The form Br2 crystal is a crystal of hydrobromide of the compound (I) and it shows the peaks appearing at angles (2 θ) of diffraction of 18.9, 20.6, 23.3, 25.0 and 26.7 and more preferably the peaks appearing at angles of diffraction of 15.6, 16.1, 18.0, 18.9, 20.6, 23.3, 25.0, 26.7, 27.7, 28.3, 31.5 and 32.8, in the powder X-ray diffraction pattern.

The form Br2 crystal can preferably be prepared by blending a mixture comprising methanol, the compound (I) and preferably acetyl bromide, preferably with ethanol, cooling the resulting mixed liquid to a temperature of preferably 5° C., and then recovering the crystals thus precipitated out of the mixed liquid. Moreover, it is also possible to obtain a desired form Br2 crystal by preparing, in advance, hydrobromide of the compound (I), blending the resulting hydrobromide with methanol and isopropanol to thus give a mixture and then repeating the same procedures used above, except for using the resulting mixture, while using ethanol, isopropanol, 2-butanone, tetrahydrofuran, methyl acetate, toluene, acetone and dichloromethane.

The form Br3 crystal is a crystal of hydrobromide of the compound (I) and it shows the peaks appearing at angles (2 θ) of diffraction of 21.53, 22.12, 23.69 and 25.39 and more preferably the peaks appearing at angles of diffraction of 12.65, 16.88, 19.74, 21.53, 22.12, 22.87, 23.69, 25.39, 26.53, 29.09 and 30.66, in the powder X-ray diffraction pattern. The form Br3 crystal can be produced by preliminarily preparing hydrobromide of the compound (I), mixing the hydrobromide with acetone to give a mixture and then repeating the same procedures used above except for using the resulting mixture.

The form Br4 crystal is a crystal of hydrobromide of the compound (I) and it shows the peaks appearing at angles (2 θ) of diffraction of 4.07, 17.78, 23.62 and 24.65 and more preferably the peaks appearing at angles of diffraction of 4.07, 15.57, 17.78, 21.17, 21.87, 22.63, 23.62, 24.65, 27.04 and 28.04, in the powder X-ray diffraction pattern. The form Br4 crystal can be produced by preliminarily preparing hydrobromide of the compound (I), mixing the resulting hydrobromide with acetonitrile to give a mixture and then repeating the same procedures used above except for using the resulting mixture.

The form Br5 crystal is a crystal of hydrobromide of the compound (I) and it shows the peaks appearing at angles (2 θ) of diffraction of 21.20, 21.98, 23.21 and 23.93 and more preferably the peaks appearing at angles of diffraction of 14.72, 17.76, 21.20, 21.98, 22.90, 23.21, 23.41, 23.93, 25.13, 28.32 and 28.81, in the powder X-ray diffraction pattern. The form Br5 crystal can be produced by preparing, in advance, hydrobromide of the compound (I), mixing the resulting hydrobromide with dimethylformamide to give a mixture and then repeating the same procedures used above except for using the resulting mixture.

The form Br6 crystal is a crystal of hydrobromide of the compound (I) and it shows the peaks appearing at angles (2 θ) of diffraction of 17.25, 23.38, 24.55 and 26.73 and more preferably the peaks appearing at angles of diffraction of 7.50, 17.25, 18.67, 18.96, 19.77, 20.72, 22.22, 23.38, 24.55, 26.73 and 28.32, in the powder X-ray diffraction pattern. The form Br6 crystal can be produced by preparing, in advance, hydrobromide of the compound (I), mixing the hydrobromide with dichloromethane to give a mixture and then repeating the same procedures used above except for using the resulting mixture.

The crystals of sulfates of the compound (I) may be those of sulfates in the form of hydrates and solvates thereof and, more specifically, examples thereof include form S1 crystals, form S2 crystals, form S3 crystals, form S4 crystals and form S5 crystals.

The form S1 crystal is a crystal of sulfate of the compound (I) and it shows the peaks appearing at angles (2 θ) of diffraction of 18.2, 22.7, 24.8 and 25.5 and more preferably the peaks appearing at angles of diffraction of 11.6, 15.3, 18.2, 19.9, 20.4, 22.7, 24.3, 24.8 and 25.5, in the powder X-ray diffraction pattern. The Form S1 crystal can preferably be produced by blending a mixture comprising methanol, the compound (I) and sulfuric acid, preferably with isopropanol and subsequently recovering the crystals precipitated out of the mixture. Alternatively, it is also possible to form a desired form S1 crystal of sulfate of the compound (I) by preparing, in advance, sulfate of the compound (I), mixing the resulting sulfate with methanol to give a mixture and then repeating the same procedures used above except for using the resulting mixture and using ethyl acetate, methyl acetate, toluene and n-heptane.

The form S2 crystal is a crystal of sulfate of the compound (I) and it shows the peaks appearing at angles (2 θ) of diffraction of 15.6, 16.2, 18.0 and 19.2 and more preferably the peaks appearing at angles of diffraction of 15.6, 16.2, 18.0, 19.2, 20.1, 22.5, 23.5 and 25.4, in the powder X-ray diffraction pattern. The form S2 crystal can preferably be produced by blending a mixture comprising methanol, the compound (I) and sulfuric acid, preferably with methyl acetate and subsequently recovering the crystals thus precipitated out of the resulting mixture. Alternatively, it is also possible to form a desired form S2 crystal of sulfate of the compound (I) by preparing, in advance, sulfate of the compound (I), mixing the resulting sulfate with methanol to give a mixture and then repeating the same procedures used above except for using the resulting mixture.

The form S3 crystal is a crystal of sulfate of the compound (I) and it shows the peaks appearing at angles (2 θ) of diffraction of 13.0, 18.7, 22.1 and 22.5 and more preferably the peaks appearing at angles of diffraction of 12.7, 13.0, 16.0, 18.7, 21.6, 22.1, 22.5 and 22.9, in the powder X-ray diffraction pattern. The form S3 crystal can preferably be produced by blending a mixture comprising methanol, the compound (I) and sulfuric acid, preferably with methyl acetate and subsequently recovering the crystals thus precipitated out of the resulting mixture. Alternatively, it is also possible to form a desired form S3 crystal of sulfate of the compound (I) by preparing, in advance, sulfate of the compound (I), mixing the resulting sulfate with methanol to give a mixture and then repeating the same procedures used above except for using the resulting mixture.

The form S4 crystal is a crystal of sulfate of the compound (I) and it shows the peaks appearing at angles (2 θ) of diffraction of 12.58, 21.08, 23.02 and 23.93 and more preferably the peaks appearing at angles (2 θ) of diffraction of 12.58, 16.87, 18.28, 21.08, 21.27, 22.79, 23.02, 23.93, 24.79 and 28.87, in the powder X-ray diffraction pattern. The form S4 crystal can be prepared by producing, in advance, sulfate of the compound (I), mixing the resulting sulfate with acetone, acetonitrile, and tetrahydrofuran to give a mixture and then repeating the same procedures used above except for using the mixture thus prepared.

The form S5 crystal is a crystal of sulfate of the compound (I) and it shows the peaks appearing at angles (2 θ) of diffraction of 4.04, 21.06, 21.46 and 25.75 and more preferably the peaks appearing at angles of diffraction of 4.04, 12.31, 18.12, 21.06, 21.46, 22.33, 23.26, 24.38, 24.99 and 25.75, in the powder X-ray diffraction pattern. The form S5 crystal can be prepared by producing, in advance, sulfate of the compound (I), mixing the resulting sulfate with ethanol to give a mixture and then repeating the same procedures used above except for using the mixture thus prepared.

The crystals of nitrate of the compound (I) may be those of the nitrate in the form of hydrates and solvates thereof and, more specifically, examples thereof include form N1 crystals and form N2 crystals.

The form N1 crystal is a crystal of nitrate of the compound (I) and it shows the peaks appearing at angles (2 θ) of diffraction of 12.8, 22.5, 23.3 and 24.6 and more preferably the peaks appearing at angles of diffraction of 11.3, 11.8, 12.8, 14.7, 21.3, 22.5, 23.3, 24.6 and 25.6, in the powder X-ray diffraction pattern. The form N1 crystal can preferably be produced by blending a mixture comprising methanol, the compound (I) and nitric acid with preferably ethanol and subsequently recovering the crystals precipitated out of the resulting mixture. Alternatively, it is also possible to form a desired form N1 crystal of nitrate of the compound (I) by preliminarily preparing nitrate of the compound (I), blending the resulting nitrate with methanol to thus give a mixture and then repeating the same procedures used above except for using the resulting mixture.

The form N2 crystal is a crystal of nitrate of the compound (I) and it shows the peaks appearing at angles (2 θ) of diffraction of 18.9, 20.7, 23.5 and 26.5 and more preferably the peaks appearing at angles of diffraction of 11.3, 15.7, 18.9, 20.7, 22.1, 23.5, 25.0, 25.4, 26.5 and 27.7, in the powder X-ray diffraction pattern. The form N2 crystal can preferably be produced by blending a mixture comprising methanol, the compound (I) and nitric acid with preferably isopropyl alcohol and subsequently recovering the crystals precipitated out of the resulting mixture. Alternatively, it is also possible to form a desired form N2 crystal of nitrate of the compound (I) by preliminarily preparing nitrate of the compound (I), blending the resulting nitrate with methanol to thus give a mixture and then repeating the same procedures used above except for using the resulting mixture.

The crystals of p-toluene-sulfonate of the compound (I) may be those of the p-toluene-sulfonate in the form of hydrates and solvates thereof and, more specifically, examples thereof include form Ts1 crystals.

The form Ts1 crystal is a crystal of p-toluene-sulfonate of the compound (I) and it shows the peaks appearing at angles (2 θ) of diffraction of 12.9, 21.5 and 23.1 and more preferably the peaks appearing at angles of diffraction of 12.9, 15.4, 17.3, 18.0, 18.2, 18.4, 20.1, 20.8, 21.0, 21.5, 21.8, 23.1 and 27.3, in the powder X-ray diffraction pattern. The Form Ts1 crystal can preferably be produced by blending a mixture of methanol, the Compound (I) and p-toluene-sulfonic acid (p-CH$_3$-Ph-SO$_3$H) with methyl acetate, ethanol, isopropyl alcohol and then recovering the crystals precipitated out of the resulting mixture. Alternatively, the form Ts1 crystal of p-toluene-sulfonate of the compound (I) can likewise be produced by preliminarily preparing p-toluene-sulfonate of the compound (I), blending the resulting p-toluene-sulfonate with methanol to thus give a mixture and then repeating the same procedures used above except for using the resulting mixture.

The crystals of methane-sulfonate of the compound (I) may be those of the methane-sulfonate in the form of hydrates and solvates thereof and, more specifically, examples thereof include forms Ms1, Ms2, Ms3 and Ms4 crystals.

The form Ms1 crystal is a crystal of methane-sulfonate of the compound (I) and it shows the peaks appearing at angles (2 θ) of diffraction of 10.1, 11.5, 21.2 and 21.9 and more preferably the peaks appearing at angles of diffraction of 10.1, 11.5, 13.1, 18.6, 19.8, 21.2, 21.9, 22.8, 23.2, 24.9, 25.3 and 31.5, in the powder X-ray diffraction pattern. The form Ms1 crystal can preferably be produced by blending a mixture of methanol, the Compound (I) and methane-sulfonic acid (CH$_3$SO$_3$H) with ethyl alcohol, acetonitrile and n-heptane, allowing the mixture to stand at a temperature of about 5° C. to obtain crystals and then recovering the resulting crystals. Alternatively, the form Ms1 crystal of methane-sulfonate of the compound (I) can likewise be produced by preliminarily preparing methanesulfonate of the compound (I), blending the resulting methane-sulfonate with methanol to thus give a mixture and then repeating the same procedures used above except for using the resulting mixture.

The form Ms2 crystal is a crystal of methane-sulfonate of the compound (I) and it shows the peaks appearing at angles (2 θ) of diffraction of 12.9, 15.9, 18.8 and 23.0 and more preferably the peaks appearing at angles of diffraction of 10.6, 12.4, 12.9, 15.9, 18.8, 19.2, 19.8, 22.2, 23.0, 23.8 and 24.3, in the powder X-ray diffraction pattern. The form Ms2 crystal can preferably be produced by blending a mixture of methanol, the Compound (I) and methane-sulfonic acid (CH$_3$SO$_3$H) with isopropyl alcohol to thus give crystals, allowing the crystals to grow or ripen by leaving them to stand at a temperature of about 5° C. and then recovering the resulting crystals. Alternatively, the form Ms2 crystal can likewise be produced by preliminarily preparing methane-sulfonate of the compound (I), blending the resulting methane-sulfonate with methanol and ethyl acetate, methyl acetate, toluene and isopropanol to thus give a mixture and then repeating the same procedures used above except for using the resulting mixture.

The form Ms3 crystal is a crystal of methane-sulfonate of the compound (I) and it shows the peaks appearing at angles (2 θ) of diffraction of 11.2, 12.6, 22.9 and 25.5 and more preferably the peaks appearing at angles of diffraction of 11.2, 12.6, 13.2, 15.8, 17.9, 20.9, 22.2, 22.9, 23.8 and 25.5, in the powder X-ray diffraction pattern. The form Ms3 crystal can preferably be produced by blending a mixture of methanol, the Compound (I) and methane-sulfonic acid (CH$_3$SO$_3$H) with ethanol, allowing the mixture to stand at room temperature (25° C.) to obtain crystals and then recovering the resulting crystals. Alternatively, the form Ms3 crystal can likewise be produced by preliminarily preparing methane-sulfonate of the compound (I), blending the resulting methane-sulfonate with methanol to thus give a mixture and then repeating the same procedures used above except for using the resulting mixture.

The form Ms4 crystal is a crystal of methane-sulfonate of the compound (I) and it shows the peaks appearing at angles (2 θ) of diffraction of 17.99, 19.22, 19.75 and 25.64 and more preferably the peaks appearing at angles of diffraction of 11.79, 12.35, 17.04, 17.99, 19.22, 19.75, 20.66, 22.64, 23.88, 25.14 and 25.64, in the powder X-ray diffraction pattern. The form Ms4 crystal can preferably be produced by blending a mixture of methanol, the Compound (I) and methane-sulfonic acid (CH$_3$SO$_3$H) with acetone, allowing the resulting mixture to stand at room temperature (25° C.) to obtain crystals and then recovering the resulting crystals. Alternatively, the form Ms4 crystal can likewise be produced by preliminarily preparing methane-sulfonate of the compound (I), blending the resulting methane-sulfonate with dichloromethane and acetone to thus give a mixture and then repeating the same procedures used above except for using the resulting mixture.

In this respect, each peak appearing at the angle (2 θ) of diffraction observed for the powder X-ray diffraction pattern may slightly undergo a change or shift depending on, for instance, the conditions for the determination thereof. Such an error may of course be acceptable even in each angle of diffraction disclosed in the instant specification.

When blending the compound (I) with an acid, in the foregoing production method, it would be sufficient that an acid such as hydrogen chloride or hydrogen bromide is added, to the compound (I), in a molar ratio, with respect to the latter, of not less than 1:1, preferably on the order of 1:1.05 to 1:2.00 and particularly preferably an acid such as hydrochloric acid is added in a molar ratio of 1:1.1.

In addition, the amount of the solvent used for the separation of desired crystals is not restricted to any specific level, but it preferably falls within the range of from 2 to 1,000 parts by mass and, in particular, 5 to 40 parts by mass, per one part by mass of the compound (in its free state) represented by the foregoing formula (I) or a salt thereof.

Moreover, in some cases, the mixed liquid comprising a salt of the compound (I) may often be left to stand or stirred for a time period preferably ranging from 30 minutes to 5 hours for the induction of crystallization of the salt of the compound (I) and/or having the precipitation of sufficient amount of the crystals.

In the production method according to the present invention, the compound (I) usable herein as a raw material may be not only one in the form of amorphous or non-crystalline solids, but also known crystals such as form a crystal.

The crystal of the present invention is not only easily used, but also excellent in its solubility as an original drug and, in particular, it is quite useful in the preparation of a pharmaceutical agent excellent in the absorbability and bioavailability. More favorably, it possesses stability sufficient for use in the production of a pharmaceutical preparation. From the foregoing standpoints, particularly preferably used herein are the forms Cl1, Br2 and Ms1 crystals of the compound (I), among the aforementioned crystalline forms, and the forms Cl1 and Br2 crystals are particularly preferred herein, with the form Cl1 being more particularly used herein.

Since the compound represented by the foregoing formula (I) or the pharmaceutically acceptable salt thereof shows an excellent α 4-integrin-inhibitory action, the crystal of the present invention can be used as an excellent α 4-integrin-inhibitory agent and it can further be effectively used as an effective component for the preparation of a therapeutic agent or a prophylactic agent for treating or preventing, for instance, either of inflammatory diseases, in which the α 4-integrin-dependent adhesion process of leucocytes is involved in the pathema thereof, rheumatoid arthritis, inflammatory intestinal diseases (inclusive of, for instance, Crohn's disease and ulcerative colitis), systemic lupus erythematosus, disseminated or multiple sclerosis, Sjogren's syndrome, asthma, psoriasis, allergy, diabetes (mellitus), cardiovascular diseases, arterial sclerosis, restenosis, tumor hyperplasia, tumor metastasis and graft rejection.

The compound represented by the foregoing formula (I) or the pharmaceutically acceptable salt thereof may likewise be used in combination with other pharmaceutical agents which can show therapeutic and/or prophylactic effects on the foregoing diseases or disorders. For instance, in case of the inflammatory intestinal diseases such as Crohn's disease and ulcerative colitis, such other pharmaceutical agents include, for instance, an elemental diet (such as Elental available from Ajinomoto Co., Ltd.), 5-ASA pharmaceutical preparations (such as mesalazine, salazosulfapyridine (sulfasalazine)), adrenocortical hormone-containing pharmaceutical preparations (such as prednisolone, bethamethasone, and budesonide), and antibacterial agents (such as metronidazole), among others. In addition, also listed as such other agents capable of being used in combination with the compound or salt of the present invention include, for instance, immunosuppressive agents (such as azathioprine, 6-mercaptoprine, ciclosporin, and tacrolimus). Moreover, anti-cytokine agents may likewise be used as such pharmaceutical agents capable of being used in combination with the foregoing. Specific examples thereof are anti-TNF α-antibodies (such as infliximab, adalimumab, certolizumab.pegol, and golimumab), anti-IL-6 receptor antibodies (such as tocilizumab), anti-IL-12/23 antibodies (such as ustekinumab, and briakinumab), anti-IL-17 receptor antibodies (such as AMG827 and AIN457), IL-12/23 production-inhibitory agents (such as STA-5326) as low molecular weight agents and PDE-4-inhibitory agents (such as tetomilast). In addition, also listed herein as such other agents include, for instance, CCR9-inhibitory agents as the cellular infiltration-inhibitory agents (such as GSK1605786 and CCX025), and anti-α 4 β 7-integrin antibodies (such as vedolizumab). Furthermore, usable herein in combination with the foregoing compounds or salts of the present invention also include other therapeutic methods which can show a therapeutic and/or prophylactic effect on the aforementioned diseases in addition to the foregoing pharmaceutical agents. For instance, in case of the inflammatory intestinal diseases such as Crohn's disease and ulcerative colitis, such therapeutic and/or prophylactic methods include, for instance, leukocyte-removing therapies (such as GCAP and LCAP).

In other words, the therapeutic or prophylactic agent used for the treatment or prevention of the foregoing diseases, which comprises the crystal of the present invention, can be used in combination with other pharmaceutical agents having an effect of treating and/or preventing the foregoing diseases. In addition, the therapeutic or prophylactic agent used for the treatment or prevention of the foregoing diseases, which comprises the crystal of the present invention, can likewise be used in combination with other therapeutic methods for the treatment of the foregoing diseases.

The pharmaceutical composition comprising the crystal according to the present invention is preferably one which comprises the crystal of the present invention in a rate of not less than that which permits the achievement of a desired and substantial therapeutic effect. The rate of the crystal, which permits the achievement of a desired and substantial therapeutic effect is determined while taking into consideration, for instance, the dose of the pharmaceutical composition and any particular therapeutic effect to be achieved, and the pharmaceutical composition can be administered through various oral or parenteral routes (through, for instance, intravenous, intra-arterial, subcutaneous, intramuscular and sublingual routes, or administered in the form of, for instance, a suppository, an enema, an ointment, a patch or a poultice, a lozenge, an eye drop or a vaporole). However, the rate of the crystal, as expressed in terms of the dose per day for adult, is generally in the range of from 1 μg to 5 g, preferably 1 mg to 1.5 g for the oral administration, while the dose per day for adults may likewise preferably range from 1 μg to 50 g, or 1 mg to 10 g, or further 1 g to 2 g. On the other hand, the crystal is used in such a rate falling within the range of from 0.01 μg to 1 g, in case of the parenteral administration.

When using the crystal of the present invention as a pharmaceutical agent, it can be used as such or in the form of a pharmaceutical composition and can be administered through, for instance, oral or parenteral routes such as intravenous, intrabuccal, per-rectal, intravaginal, percutaneous or intra-nasal routes, or through inhalation, but the pharmaceutical agent is preferably be administrated orally. The pharmaceutical composition to be orally administered may be in the form of, for instance, tablets (including, for instance, sugarcoated tablets, coating tablets, dry coated tablets, and sublingual tablets), pills, capsules (including, for instance, hard capsules, soft capsules and microcapsules), powders, granules, fine granules, troches, and liquid preparations (including, for instance, syrup, emulsions and suspensions).

Such a pharmaceutical agent can be prepared according to any method commonly used in this art after, for instance, blending the crystal of the present invention with, for instance, pharmaceutically acceptable excipients and carriers.

Examples of such pharmaceutically acceptable excipients and carriers include excipients, binders, disintegrators and/or lubricants currently used in the production of solid pharmaceutical preparations; and solvents, solubilizing agents, suspending agents, buffering agents, thickeners, and emulsifying agents used in the production of liquid pharmaceutical preparations. Moreover, it is also possible to use additives for pharmaceutical preparations such as coloring agents, antioxidants and/or sweetening agents, as the need arises.

In respect of, for instance, the tablets, granules and fine granules, they may be coated with any known coating agent according to any known method, for the purposes of, for instance, the masking of the taste thereof, the improvement of the stability thereof to light, and/or the impartment of the enteric characteristics thereto. Examples of such coating agents usable herein include sugar-coating materials, water-soluble film-coating materials, and enteric film-coating materials.

EXAMPLES

The present invention will hereunder be described in more specifically. Illustrative methods for the preparation of the crystal according to the present invention will be described below with reference to the following Examples, but the present invention is not restricted to these specific Examples at all.

Example 1

Production of Form Cl1 Crystal

The compound (I) (500 mg) in its free form was suspended in 2 mL of methanol, 79 µL of methanol containing 2 moles of hydrogen chloride was added to the resulting suspension and then the mixture was stirred at room temperature for the dissolution of the compound (I). This methanol solution was dropwise added to 2 mL of isopropyl alcohol, the crystals thus precipitated out of the mixture was separated, and then the crystals were dried at 50° C. under reduced pressure to thus give 573 mg of the intended crystal (form Cl1 crystals) of hydrochloride of the compound (I) as a pale green solid.

Example 1-2

Production of Form Cl1 Crystal

To 50.0 g of the compound (I) in its free form, there was added 88 mL of methanol containing 2 moles of hydrogen chloride and then the resulting mixture was stirred at room temperature for the dissolution of the compound (I). This methanol solution was dropwise added to 625 mL of ethanol, the resulting mixture was then stirred at room temperature for 2 hours and subsequently, the mixture was allowed to stand overnight in a refrigerator. After the separation of the crystals thus precipitated out of the mixture, they were dried at 50° C. under reduced pressure and the moisture content thereof was subsequently controlled at a temperature of 50° C. to give 51.97 g of the intended crystals (form Cl1 crystals) of hydrochloride of the compound (I) as a pale green solid.

Powder X-Ray Diffraction Pattern: FIG. 1

$^1$H-NMR (DMSO-$d_6$): δ 2.99-3.27 (dd, 2H), 3.08 (s, 6H), 3.53 (s, 3H), 3.69 (s, 3H), 4.79-4.85 (m, 1H), 7.20 (d, 2H), 7.38-7.47 (m, 5H), 7.56 (d, 1H), 7.74 (b, 2H), 9.28 (d, 1H)

Mass (ESI, Found Value): [M+H]$^+$ 568.9

IC (Determined as Cl Anion, Found Value): 5.1 w/w % (as HCl)

Example 2

Production of Form Cl2 Crystal

There were suspended 10 g of the crystals of hydrochloride of the compound (I) in 700 mL of ethanol, and then the resulting suspension was stirred at 65° C. so that the compound (I) was dissolved in the solvent. This ethanol solution was cooled down to 5° C. while stirring the solution, the crystals thus precipitated out of the solution was separated and subsequently the crystals were dried at 40° C. under reduced pressure to thus give 9.72 g of the intended crystals (form Cl2 crystals) of hydrochloride of the compound (I) as a white solid.

Figure 2:
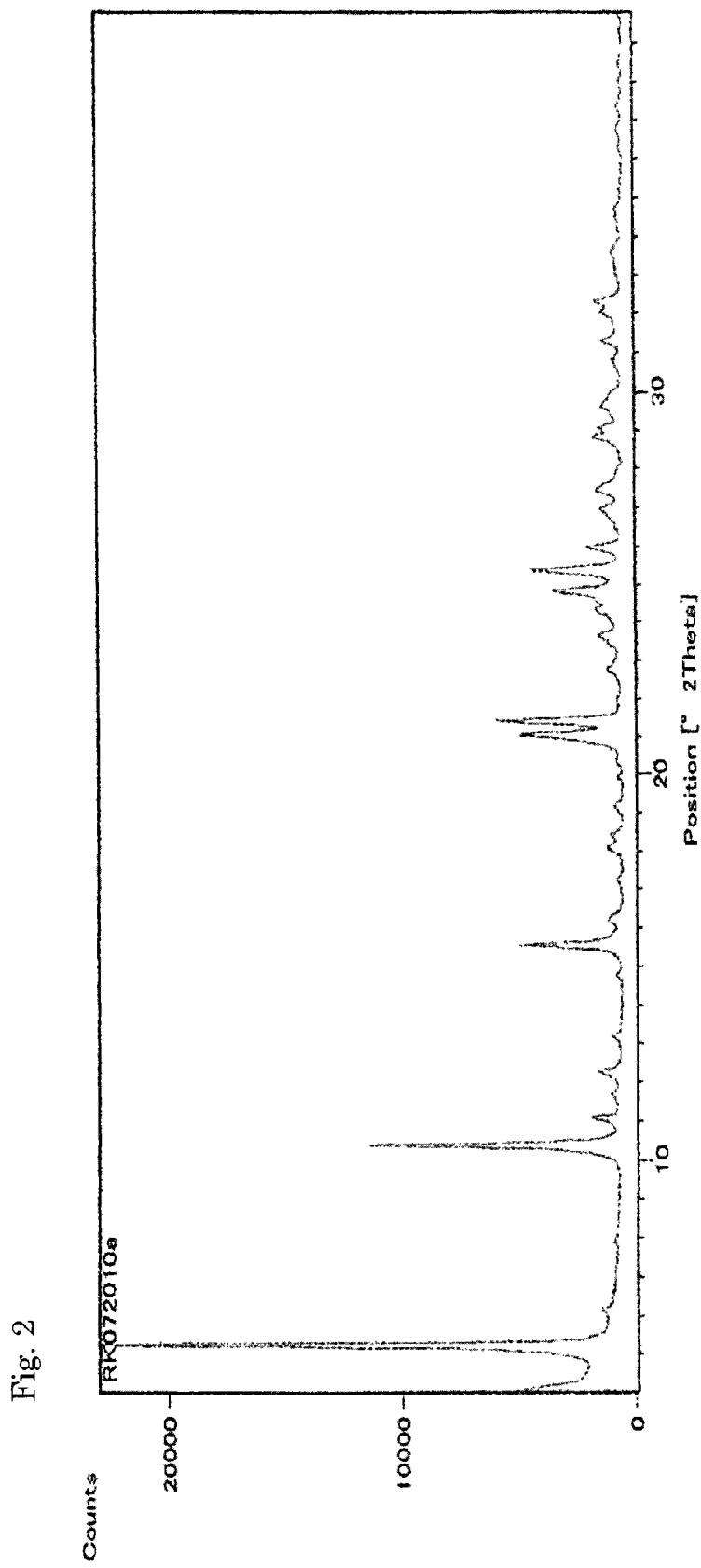
FIG. 2 is a diagram showing the powder X-ray diffraction pattern observed for the form Cl 2 crystal according to the present invention wherein the angle of diffraction: 2 θ (degrees) is plotted as abscissa, while the intensity (counts) is plotted as ordinate.

Powder X-Ray Diffraction Pattern: FIG. 2

$^1$H-NMR (DMSO-$d_6$): δ 2.99-3.25 (dd, 2H), 3.10 (s, 6H), 3.53 (s, 3H), 3.69 (s, 3H), 4.79-4.82 (m, 1H), 7.20 (d, 2H), 7.38-7.47 (m, 5H), 7.58 (d, 1H), 8.02 (b, 2H), 9.28 (d, 1H);

Mass (ESI, Found Value): [M+H]$^+$ 568.9

IC (Determined as Cl Anion, Found Value): 5.5 w/w % (as HCl)

Example 3

Production of Form Cl3 Crystal

There were dissolved 10 g of the crystals of hydrochloride of the compound (I) in a mixed solvent containing 40 mL of methanol and 140 mL of acetone, while stirring these substances at room temperature for the dissolution of the compound (I). This mixed solution was dropwise added to 40 mL of acetone with stirring, the crystals thus precipitated out of the mixed solution was separated and subsequently the crystals were dried at 40° C. under reduced pressure to thus give 2.81 g of the intended crystals (form Cl3 crystals) of hydrochloride of the compound (I) as a pale green solid.

Figure 3:
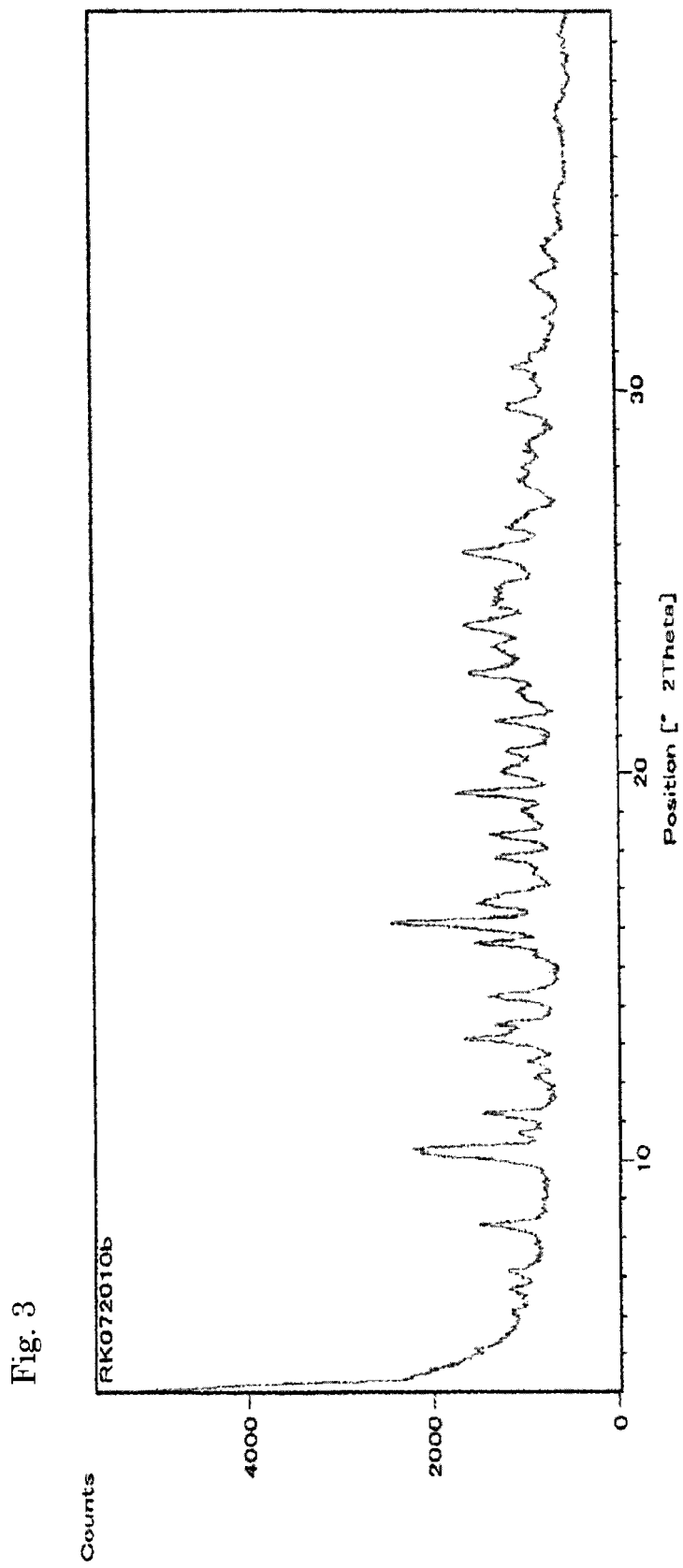
FIG. 3 is a diagram showing the powder X-ray diffraction pattern observed for the form Cl 3 crystal according to the present invention wherein the angle of diffraction: 2 θ (degrees) is plotted as abscissa, while the intensity (counts) is plotted as ordinate.

Powder X-Ray Diffraction Pattern: FIG. 3

$^1$H-NMR (DMSO-$d_6$): δ 2.89-3.22 (dd, 2H), 3.08 (s, 6H), 3.53 (s, 3H), 3.69 (s, 3H), 4.79-4.82 (m, 1H), 7.20 (d, 2H), 7.39-7.47 (m, 5H), 7.57 (d, 1H), 7.87 (b, 2H), 9.28 (d, 1H)

Mass (ESI, Found Value): [M+H]$^+$ 568.9

IC (Determined as Cl Anion, Found Value): 5.5 w/w % (as HCl)

Example 4

Production of Form Cl4 Crystal

To 5 mL of acetonitrile, there were added 500 mg of the crystals of hydrochloride of the compound (I) and the mixture was stirred at room temperature to thus form a suspension. The resulting precipitates were separated from the suspension and then dried at 40° C. under reduced pressure to thus give 501 mg of the intended crystals (form Cl4 crystals) of hydrochloride of the compound (I) as a pale green solid.

Figure 4:
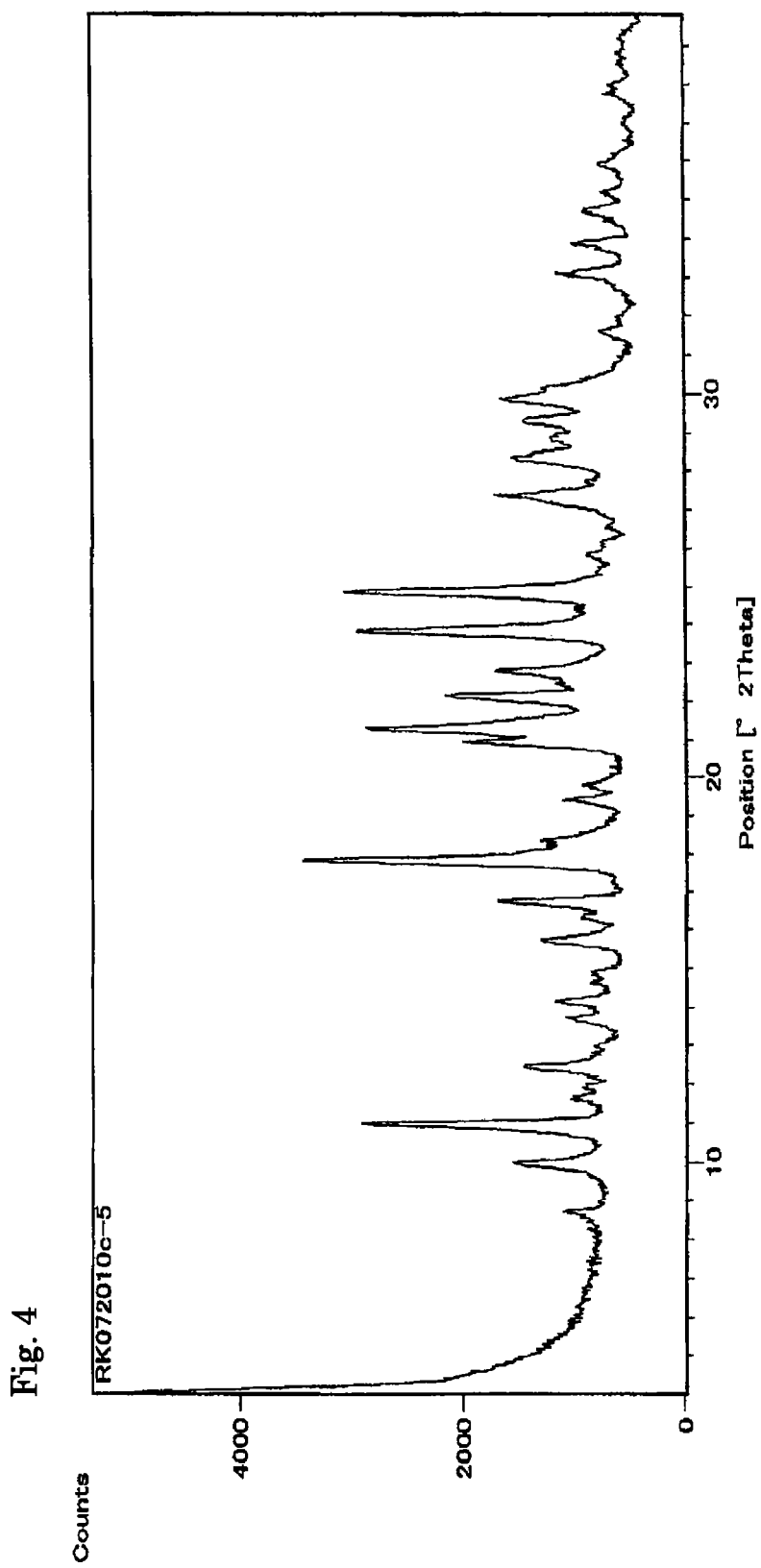
FIG. 4 is a diagram showing the powder X-ray diffraction pattern observed for the form Cl 4 crystal according to the present invention wherein the angle of diffraction: 2 θ (degrees) is plotted as abscissa, while the intensity (counts) is plotted as ordinate.

Powder X-Ray Diffraction Pattern: FIG. 4
$^1$H-NMR (DMSO-d$_6$): δ 2.99-3.25 (dd, 2H), 3.09 (s, 6H), 3.53 (s, 3H), 3.69 (s, 3H), 4.79-4.85 (m, 1H), 7.20 (d, 2H), 7.38-7.47 (m, 5H), 7.59 (d, 1H), 7.98 (b, 2H), 9.28 (d, 1H)
Mass (ESI, Found Value): [M+H]$^+$ 568.9
IC (Determined as Cl Anion, Found Value): 5.2 w/w % (as HCl)

Example 5

Production of Form Cl5 Crystal

Figure 5:
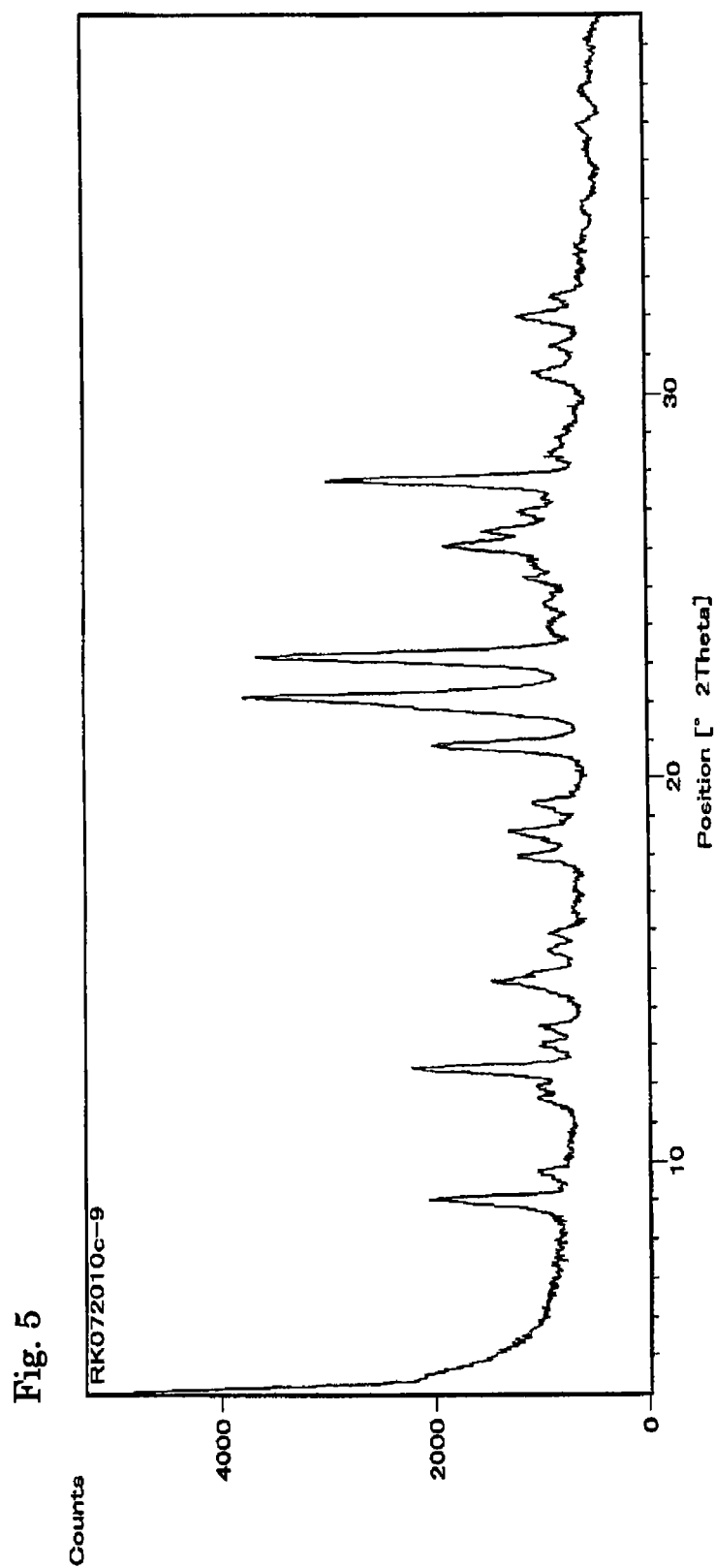
FIG. 5 is a diagram showing the powder X-ray diffraction pattern observed for the form Cl 5 crystal according to the present invention wherein the angle of diffraction: 2 θ (degrees) is plotted as abscissa, while the intensity (counts) is plotted as ordinate.

There was suspended 10 g of the compound (I) in its free state in 50 mL of methyl acetate at 50° C., then 35 mL of ethyl acetate containing one mole of hydrogen chloride was added to the suspension and the resulting mixture was stirred at 50° C. for the dissolution of the compound (I). The resulting mixed solution was cooled down to 10° C., the crystals precipitated out of the solution was removed and then dried at 40° C. under reduced pressure to give the intended crystals (form Cl5 crystals) of hydrochloride of the compound (I) as a white solid.
Powder X-Ray Diffraction Pattern: FIG. 5
$^1$H-NMR (DMSO-d$_6$): δ 2.99-3.25 (dd, 2H), 3.08 (s, 6H), 3.53 (s, 3H), 3.69 (s, 3H), 4.79-4.82 (m, 1H), 7.20 (d, 2H), 7.39-7.47 (m, 5H), 7.57 (d, 1H), 7.85 (b, 2H), 9.28 (d, 1H)
Mass (ESI, Found Value): [M+H]$^+$ 568.9
IC (Determined as Cl Anion, Found Value): 5.7 w/w % (as HCl)

Example 6

Production of Form Cl6 Crystal

Figure 6:
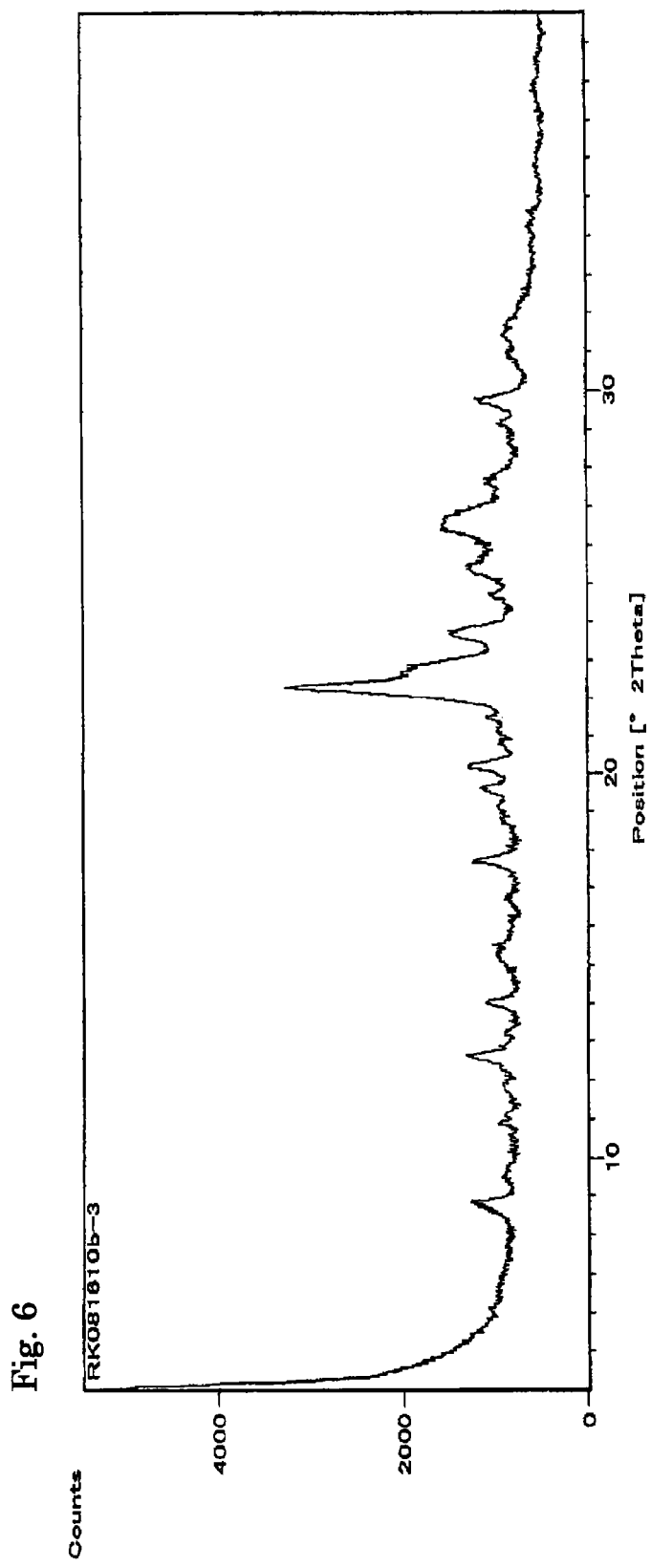
FIG. 6 is a diagram showing the powder X-ray diffraction pattern observed for the form Cl 6 crystal according to the present invention wherein the angle of diffraction: 2 θ (degrees) is plotted as abscissa, while the intensity (counts) is plotted as ordinate.

There were added 500 mg of the crystals of hydrochloride of the compound (I) to a mixture comprising 3 mL of acetonitrile and 3 mL of methyl acetate and the mixture was stirred at room temperature to form a suspension. The precipitates thus separated out of the mixture was removed and then dried at 40° C. under reduced pressure to thus give 18.9 mg of the intended crystals (form Cl6 crystals) of hydrochloride of the compound (I) as a pale green solid.
Powder X-Ray Diffraction Pattern: FIG. 6
$^1$H-NMR (DMSO-d$_6$): δ 2.99-3.25 (dd, 2H), 3.09 (s, 6H), 3.53 (s, 3H), 3.70 (s, 3H), 4.79-4.85 (m, 1H), 7.20 (d, 2H), 7.38-7.47 (m, 5H), 7.58 (d, 1H), 7.88 (b, 2H), 9.28 (d, 1H)
Mass (ESI, Found Value): [M+H]$^+$ 568.9
IC (Determined as Cl Anion, Found Value): 5.7 w/w % (as HCl)

Example 7

Production of Form Cl7 Crystal

Figure 7:
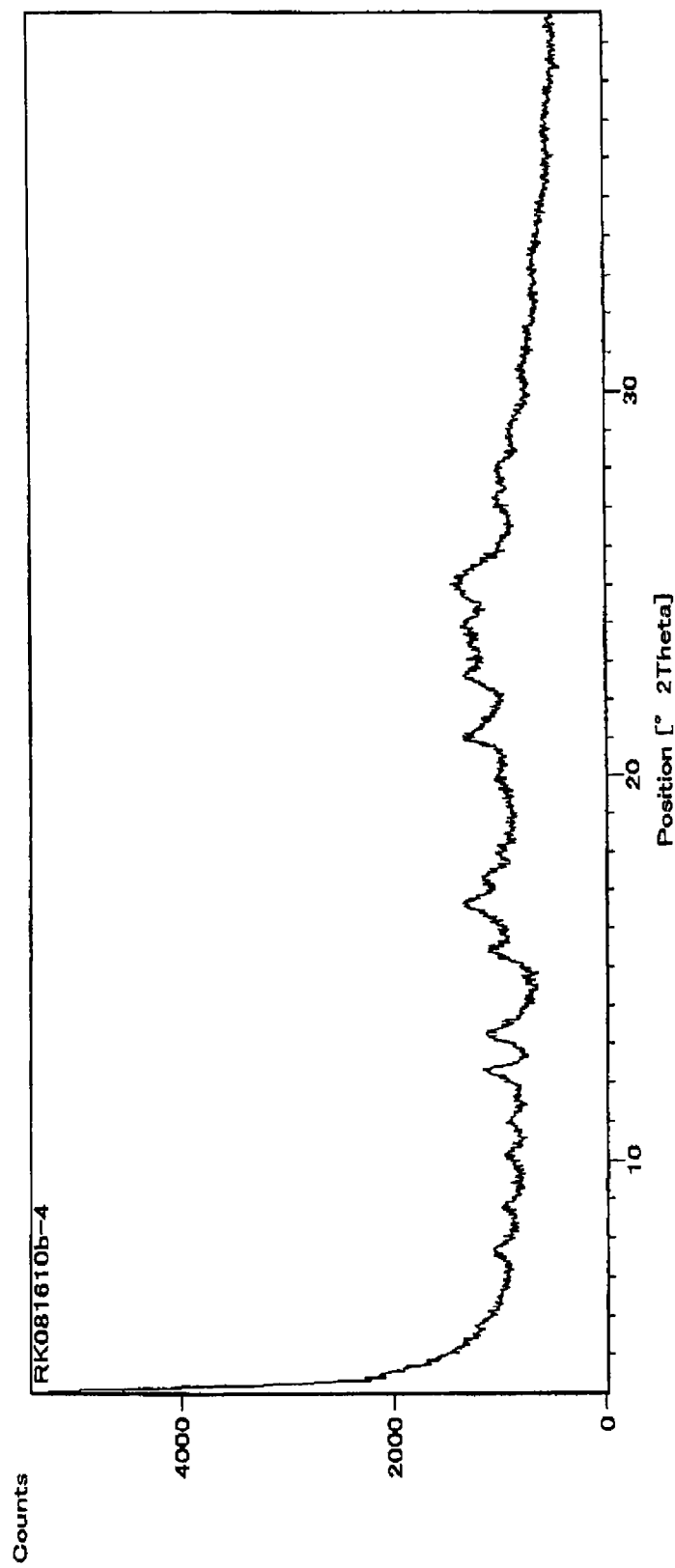
FIG. 7 is a diagram showing the powder X-ray diffraction pattern observed for the form Cl 7 crystal according to the present invention wherein the angle of diffraction: 2 θ (degrees) is plotted as abscissa, while the intensity (counts) is plotted as ordinate.

To a mixture of 5 mL of isopropanol and 5 mL of tetrahydrofuran, there were added 500 mg of the crystals of hydrochloride of the compound (I) and the mixture was then stirred at room temperature to give a suspension. The suspended material was separated from the suspension and then dried at 40° C. under reduced pressure to give 420.3 mg of the intended crystals (form Cl7 crystals) of hydrochloride of the compound (I) as a pale green solid.
Powder X-Ray Diffraction Pattern: FIG. 7
$^1$H-NMR (DMSO-d$_6$): δ 2.99-3.25 (dd, 2H), 3.10 (s, 6H), 3.53 (s, 3H), 3.69 (s, 3H), 4.79-4.85 (m, 1H), 7.20 (d, 2H), 7.38-7.47 (m, 5H), 7.60 (d, 1H), 7.98 (b, 2H), 9.28 (d, 1H)
Mass (ESI, Found Value): [M+H]$^+$ 568.9
IC (Determined as Cl Anion, Found Value): 5.8 w/w % (as HCl)

Example 8

Production of Form Br1 Crystal

Figure 8:
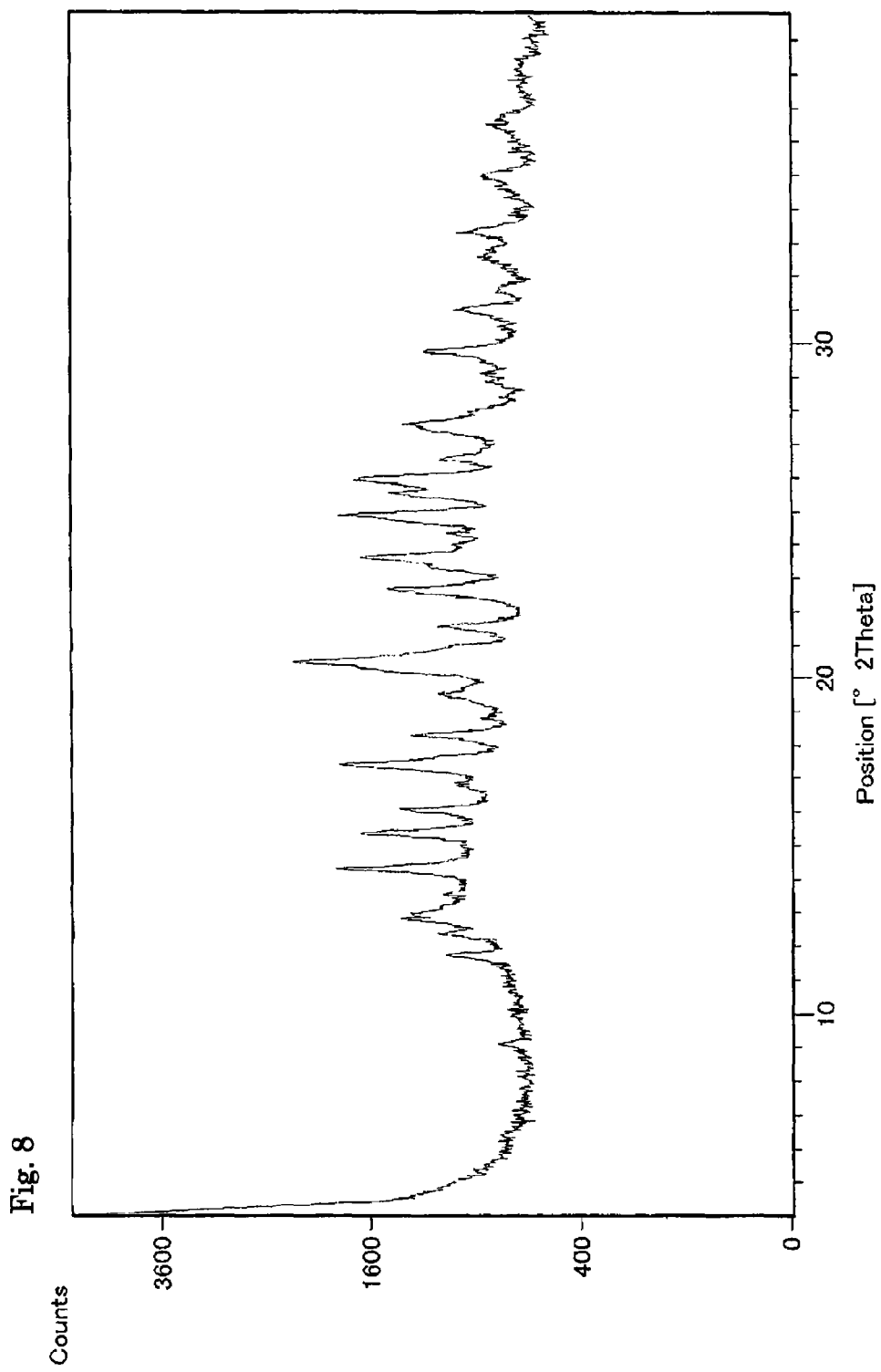
FIG. 8 is a diagram showing the powder X-ray diffraction pattern observed for the form Br1 crystal according to the present invention wherein the angle of diffraction: 2 θ (degrees) is plotted as abscissa, while the intensity (counts) is plotted as ordinate.

There was suspended, in 35 mL of methanol, 5.1 g of the compound (I) in its free state and the suspension was cooled in an ice bath. The compound (I) was dissolved by the addition of 955 μL of acetyl bromide with stirring. Crystals were precipitated out of the solution when allowing the methanol solution to stand at room temperature. The crystals thus separated were recovered, washed with methanol and then dried at 60° C. under reduced pressure to thus give 0.89 g of the intended crystals (form Br1 crystals) of hydrobromide of the compound (I) as a white solid.
Powder X-Ray Diffraction Pattern: FIG. 8
$^1$H-NMR (DMSO-d$_6$): δ 2.99-3.25 (dd, 2H), 3.10 (s, 6H), 3.53 (s, 3H), 3.69 (s, 3H), 4.79-4.85 (m, 1H), 7.19 (d, 2H), 7.39-7.47 (m, 5H), 7.55 (d, 1H), 7.74 (b, 2H), 9.27 (d, 1H)
Mass (ESI, Found Value): [M+H]$^+$569.1
IC (Determined as Br Anion, Found Value): 11.6 w/w % (as HBr)

Example 9

Production of Form Br2 Crystal

Figure 9:
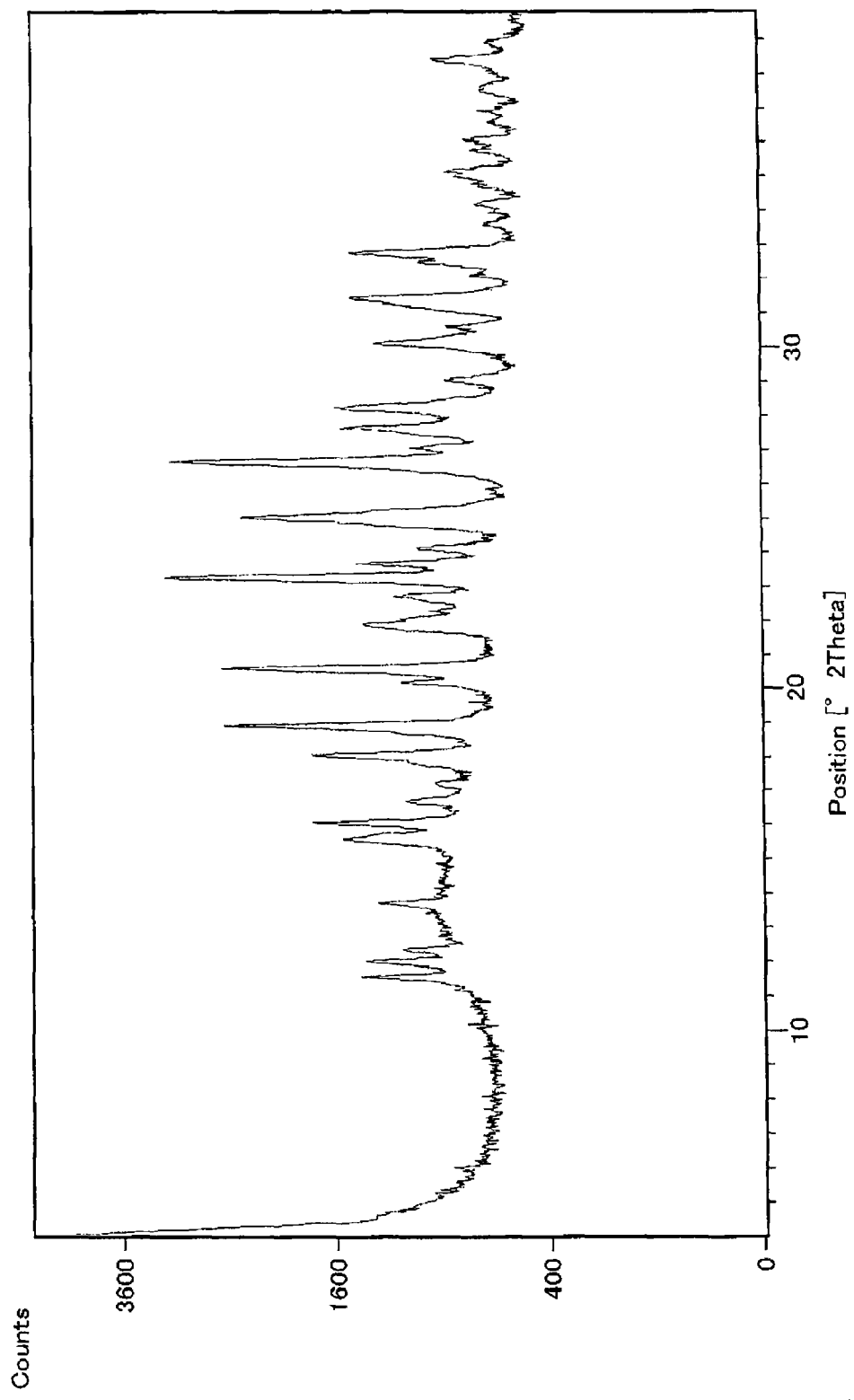
FIG. 9 is a diagram showing the powder X-ray diffraction pattern observed for the form Br2 crystal according to the present invention wherein the angle of diffraction: 2 θ (degrees) is plotted as abscissa, while the intensity (counts) is plotted as ordinate.

There were suspended, in 7 mL of methanol, 1.0 g of the compound (I) in the free state, 191 μL of acetyl bromide was added to the suspension and then the mixture was stirred at room temperature for the dissolution of the compound (I). Thereafter, the solution was dropwise added to 20 mL of ethyl alcohol and the mixture was allowed to stand in a refrigerator (about 4° C.). The crystals thus precipitated out of the mixture, washed with 10 mL of ethanol and then dried at 50° C. under reduced pressure to thus give 1.04 g of the intended crystals (form Br2 crystals) of hydrobromide of the compound (I) as a pale green solid.
Powder X-Ray Diffraction Pattern: FIG. 9
$^1$H-NMR (DMSO-d$_6$): δ 3.03-3.22 (dd, 2H), 3.13 (s, 6H), 3.53 (s, 3H), 3.69 (s, 3H), 4.79-4.85 (m, 1H), 7.20 (d, 2H), 7.38-7.47 (m, 5H), 7.59 (d, 1H), 7.87 (b, 2H), 9.28 (d, 1H)
Mass (ESI, Found Value): [M+H]$^+$ 569.0
IC (Determined as Br Anion, Found Value): 12.3 w/w % (as HBr)

Example 10

Production of Form Br3 Crystal

Figure 10:
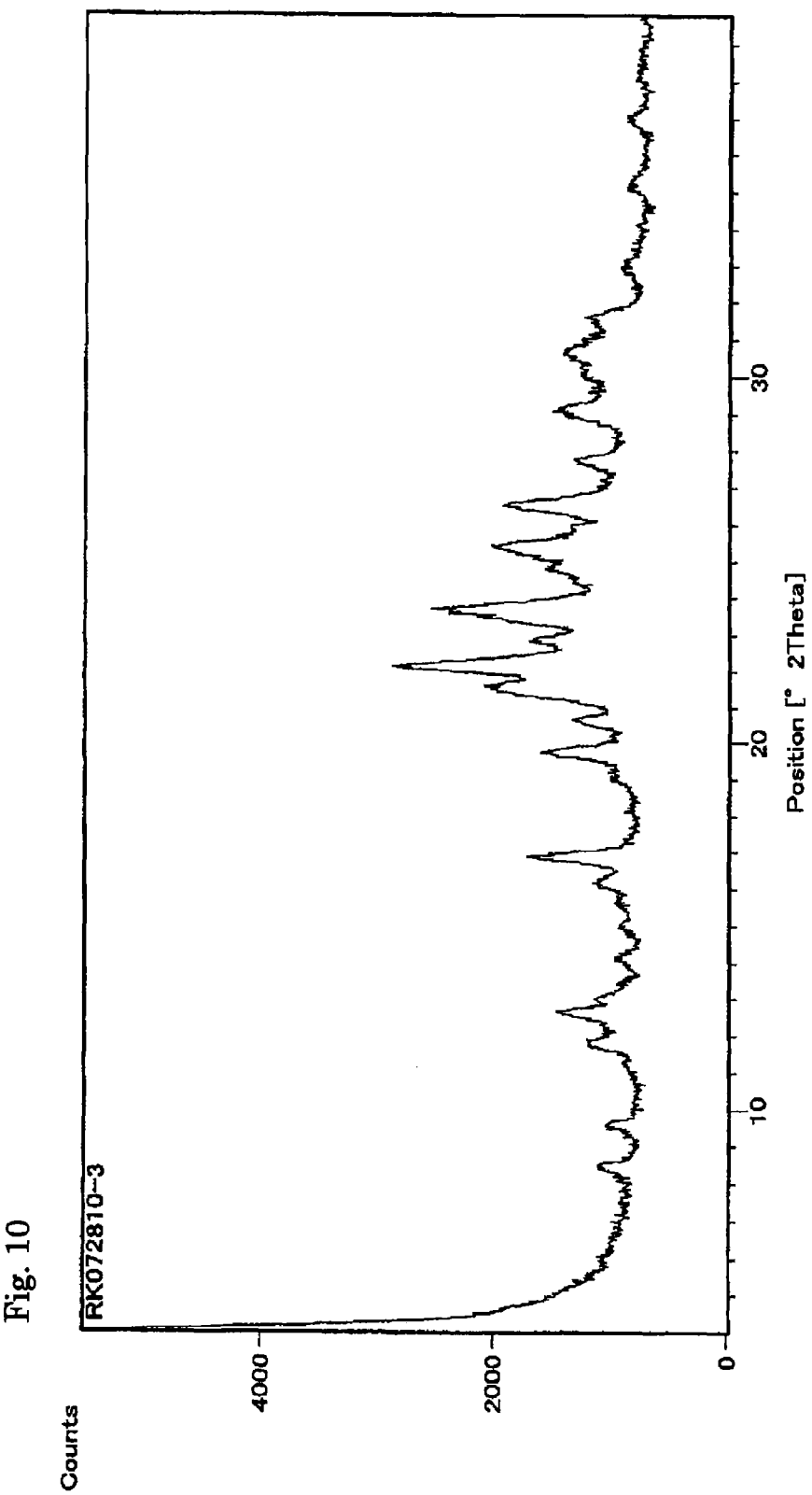
FIG. 10 is a diagram showing the powder X-ray diffraction pattern observed for the form Br3 crystal according to the present invention wherein the angle of diffraction: 2 θ (degrees) is plotted as abscissa, while the intensity (counts) is plotted as ordinate.

To 8 mL of acetone, there were added 500 mg of the crystals of hydrobromide of the compound (I) and the mixture was stirred at room temperature to give a suspension. The suspended material was removed from the suspension and then dried at 40° C. under reduced pressure to thus give 459.2 mg of the intended crystals (form Br3 crystals) of hydrobromide of the compound (I) as a pale green solid.
Powder X-Ray Diffraction Pattern: FIG. 10
$^1$H-NMR (DMSO-d$_6$): δ 3.00-3.26 (dd, 2H), 3.13 (s, 6H), 3.53 (s, 3H), 3.69 (s, 3H), 4.79-4.85 (m, 1H), 7.20 (d, 2H), 7.38-7.46 (m, 5H), 7.59 (d, 1H), 7.85 (b, 2H), 9.28 (d, 1H)
Mass (ESI, Found Value): [M+H]$^+$ 568.9
IC (Determined as Br Anion, Found Value): 11.5 w/w % (as HBr)

Example 11

Production of Form Br4 Crystal

To 5 mL of acetonitrile, there were added 500 mg of the crystals of hydrobromide of the compound (I) and the mixture was stirred at room temperature to give a suspension. The suspended material was removed from the suspension and then dried at 40° C. under reduced pressure to thus give 528.6 mg of the intended crystals (form Br4 crystals) of hydrobromide of the compound (I) as a pale green solid.

Figure 11:
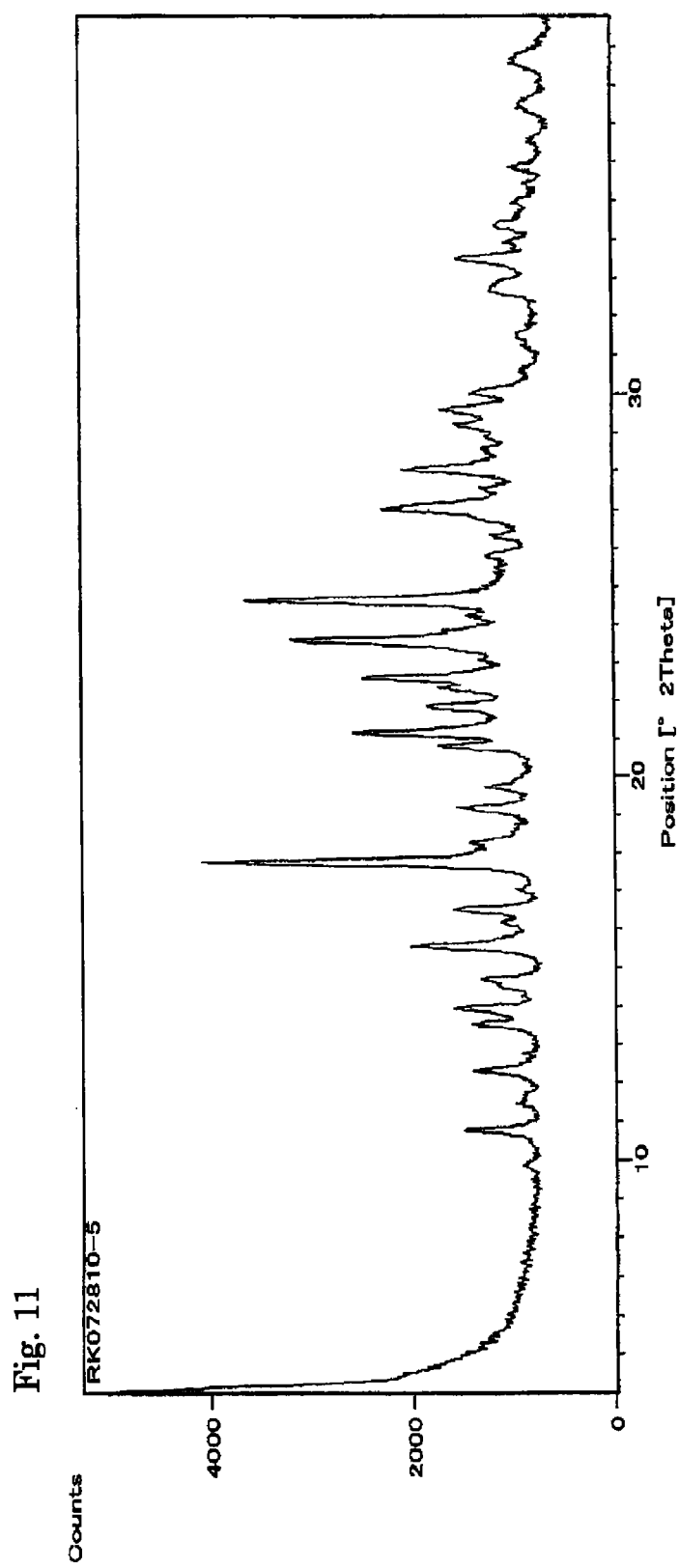
FIG. 11 is a diagram showing the powder X-ray diffraction pattern observed for the form Br4 crystal according to the present invention wherein the angle of diffraction: 2 θ (degrees) is plotted as abscissa, while the intensity (counts) is plotted as ordinate.

Powder X-Ray Diffraction Pattern: FIG. 11

$^1$H-NMR (DMSO-d$_6$): δ 3.00-3.25 (dd, 2H), 3.14 (s, 6H), 3.53 (s, 3H), 3.70 (s, 3H), 4.79-4.85 (m, 1H), 7.20 (d, 2H), 7.38-7.47 (m, 5H), 7.59 (d, 1H), 7.88 (b, 2H), 9.28 (d, 1H)

Mass (ESI, Found Value): [M+H]$^+$ 568.9

IC (Determined as Br Anion, Found Value): 10.9 w/w % (as HBr)

Example 12

Production of Form Br5 Crystal

The crystals of hydrobromide of the compound (I) (2 g) were added to 1 mL of dimethylformamide and the mixture was stirred at room temperature to form a suspension. After the separation of the suspended material, the latter was dried at 40° C. under reduced pressure to thus give 2.23 g of the intended crystals (form Br5 crystals) of hydrobromide of the compound (I) as a pale green solid.

Figure 12:
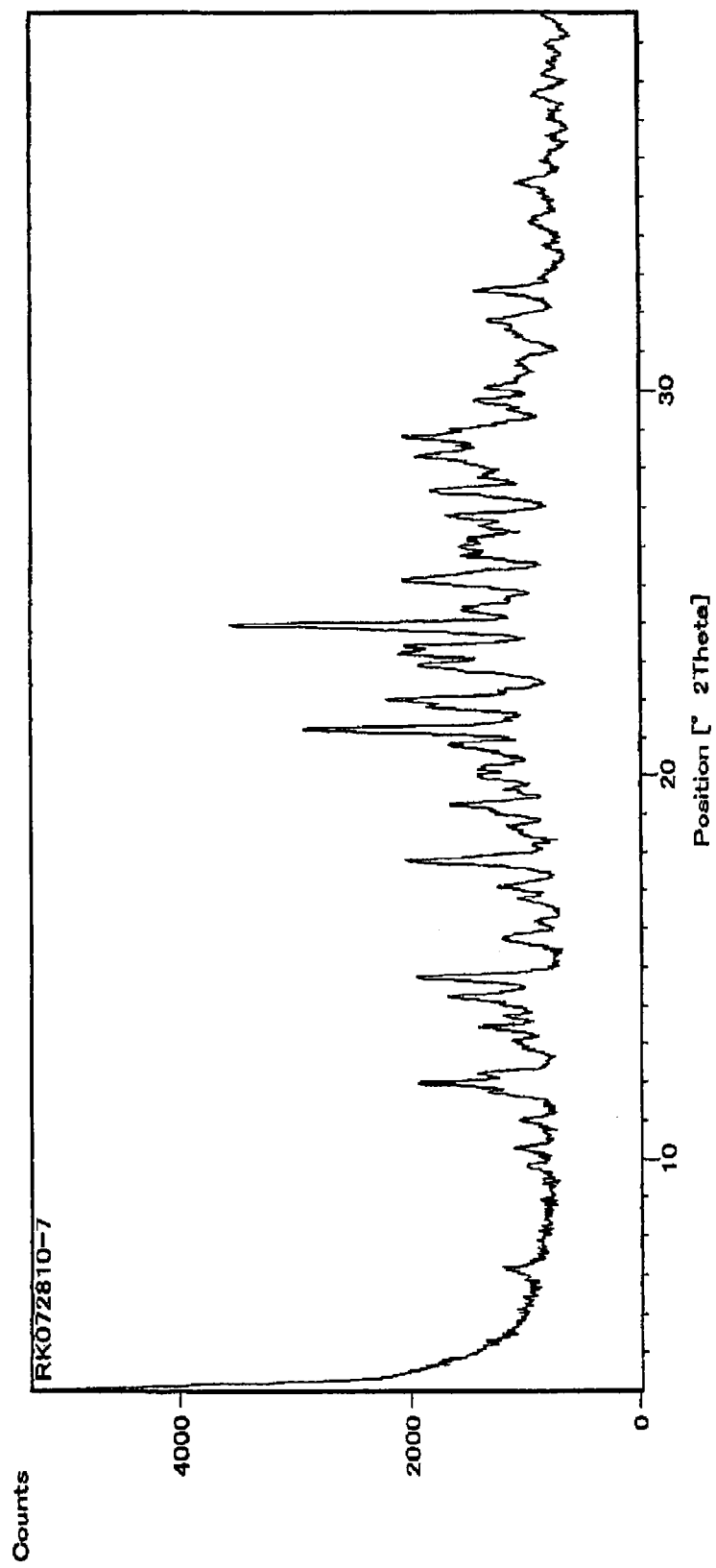
FIG. 12 is a diagram showing the powder X-ray diffraction pattern observed for the form Br5 crystal according to the present invention wherein the angle of diffraction: 2 θ (degrees) is plotted as abscissa, while the intensity (counts) is plotted as ordinate.

Powder X-Ray Diffraction Pattern: FIG. 12

$^1$H-NMR (DMSO-d$_6$): δ 3.03-3.25 (dd, 2H), 3.12 (s, 6H), 3.53 (s, 3H), 3.70 (s, 3H), 4.79-4.85 (m, 1H), 7.19 (d, 2H), 7.38-7.47 (m, 5H), 7.57 (d, 1H), 7.84 (b, 2H), 9.28 (d, 1H)

Mass (ESI, Found Value): [M+H]$^+$ 568.9

IC (Determined as Br Anion, Found Value): 9.9 w/w % (as HBr)

Example 13

Production of Form Br6 Crystal

The compound (I) (10 g) in its free state was suspended in 1 mL of methanol, then 1.95 mL of acetyl bromide was added to the suspension and the mixture was stirred at room temperature for the dissolution of the compound (I). Thereafter, the solution was dropwise added to 90 mL of dichloromethane and the resulting mixture was stirred at 10° C. to precipitate crystals. The crystals thus precipitated out of the solution were separated, washed with 60 mL of dichloromethane and finally dried at 40° C. under reduced pressure to give 10.5 g of the title crystals (form Br6 crystals) of hydrobromide of the compound (I) as a white solid.

Figure 13:
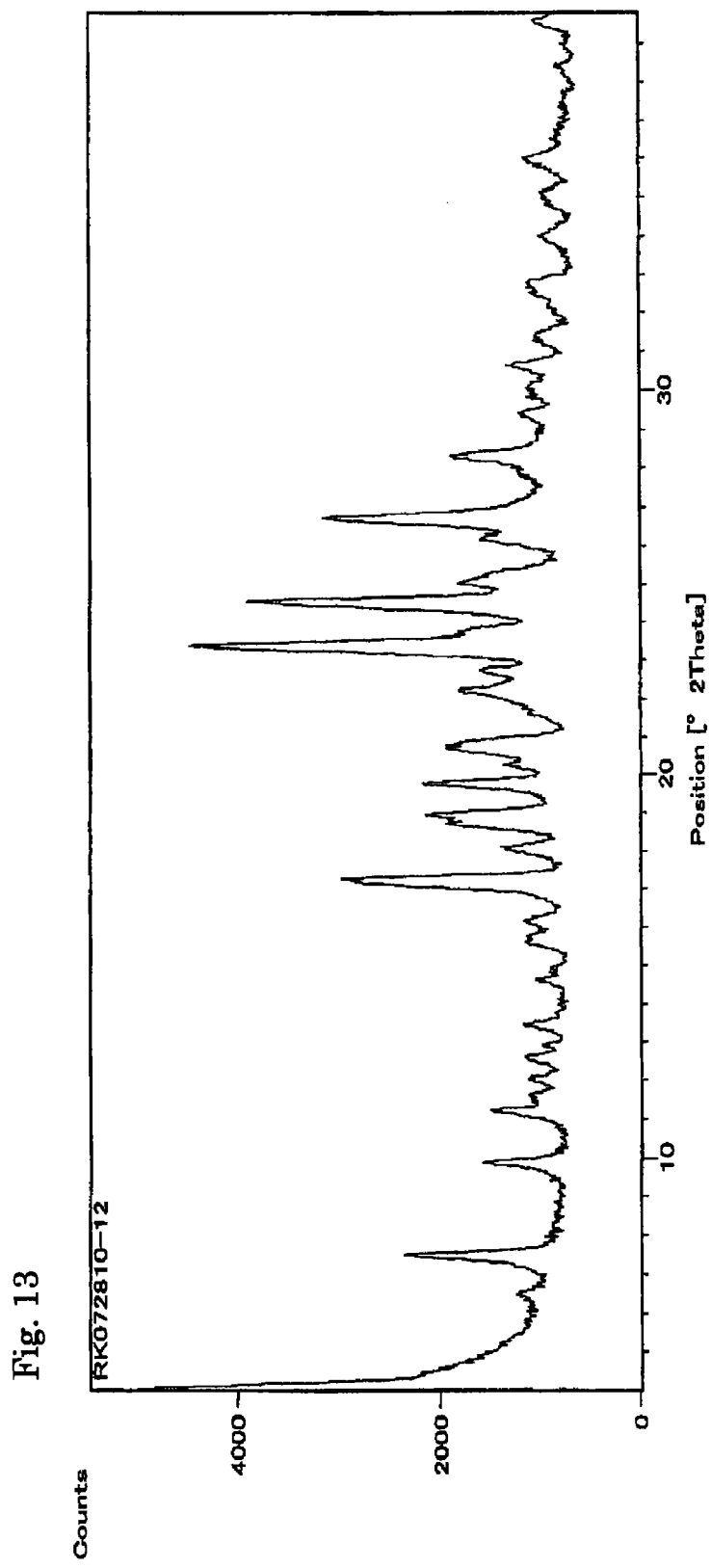
FIG. 13 is a diagram showing the powder X-ray diffraction pattern observed for the form Br6 crystal according to the present invention wherein the angle of diffraction: 2 θ (degrees) is plotted as abscissa, while the intensity (counts) is plotted as ordinate.

Powder X-Ray Diffraction Pattern: FIG. 13

$^1$H-NMR (DMSO-d$_6$): δ 2.99-3.25 (dd, 2H), 3.09 (s, 6H), 3.52 (s, 3H), 3.70 (s, 3H), 4.79-4.85 (m, 1H), 7.20 (d, 2H), 7.38-7.47 (m, 5H), 7.59 (d, 1H), 7.87 (b, 2H), 9.28 (d, 1H)

Mass (ESI, Found Value): [M+H]$^+$ 568.9

IC (Determined as Br Anion, Found Value): 11.3 w/w % (as HBr)

Example 14

Production of Form S1 Crystal

There was suspended, in 1 mL of methanol, 500 mg of the compound (I) in the free state, then 50 µL of sulfuric acid was added to the suspension and the mixture was stirred at room temperature for the dissolution of the compound (I). Subsequently, the resulting solution was dropwise added to 3 mL of isopropyl alcohol to thus precipitate crystals. The crystals thus precipitated out of the solution were removed and then dried at 60° C. under reduced pressure to give 408 mg of the title crystals (form S1 crystals) of sulfate of the compound (I) as a solid.

Figure 14:
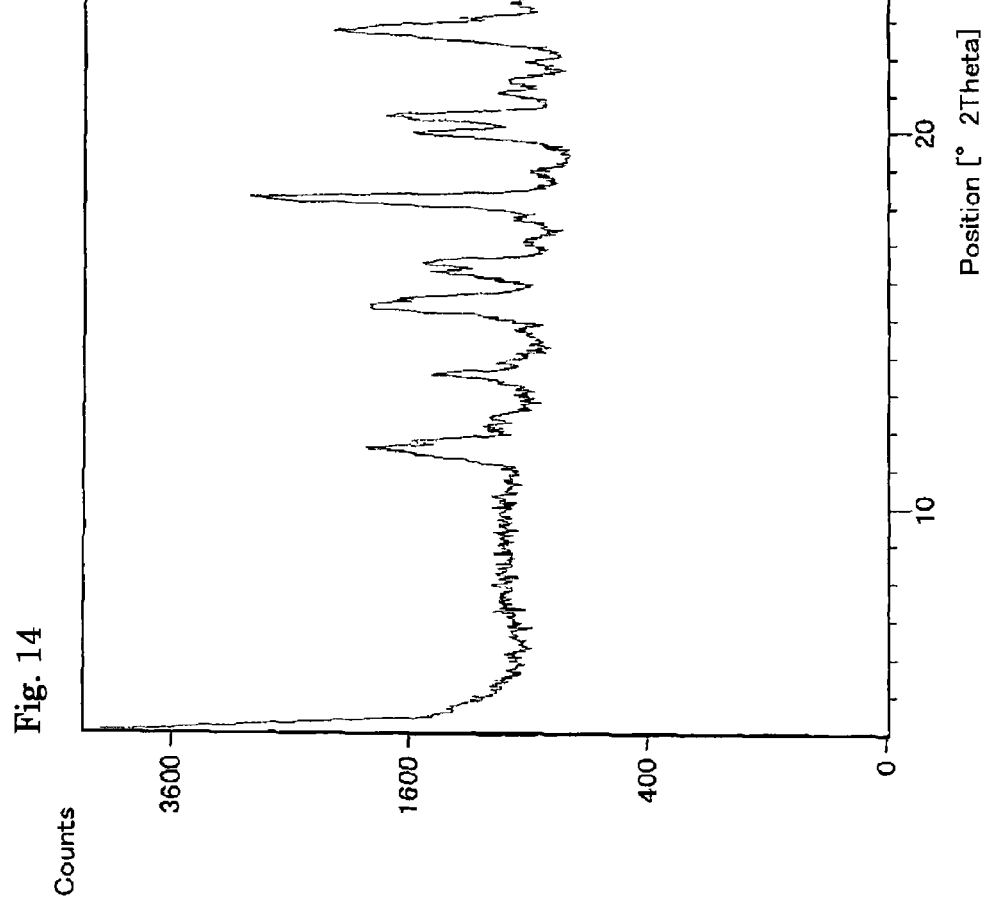
FIG. 14 is a diagram showing the powder X-ray diffraction pattern observed for the form S1 crystal according to the present invention wherein the angle of diffraction: 2 θ (degrees) is plotted as abscissa, while the intensity (counts) is plotted as ordinate.

Powder X-Ray Diffraction Pattern: FIG. 14

$^1$H-NMR (DMSO-d$_6$): δ 2.99-3.25 (dd, 2H), 3.09 (s, 6H), 3.52 (s, 3H), 3.69 (s, 3H), 4.79-4.85 (m, 1H), 7.14 (d, 2H), 7.38-7.47 (m, 5H), 7.53 (d, 1H), 7.69 (b, 2H), 7.70-8.50 (b, 2H), 9.27 (d, 1H)

Mass (ESI, Found Value): [M+H]$^+$ 568.9

IC (Determined as SO$_4$ Anion, Found Value): 14.4 w/w % (as H$_2$SO$_4$)

Example 15

Production of Form S2 Crystal

The compound (I) (5.0 g) in its free state was suspended in 10 mL of methanol, then 500 µL of sulfuric acid was added to the suspension and the mixture was stirred at room temperature for the dissolution of the compound (I). Thereafter, the resulting solution was dropwise added to 100 mL of methyl acetate and 50 mL of additional methyl acetate was added to the mixture to thus precipitate crystals. The crystals thus precipitated out of the mixture were separated and then dried at 60° C. under reduced pressure to thus give 5.0 g of the title crystals (form S2 crystals) of sulfate of the compound (I).

Figure 15:
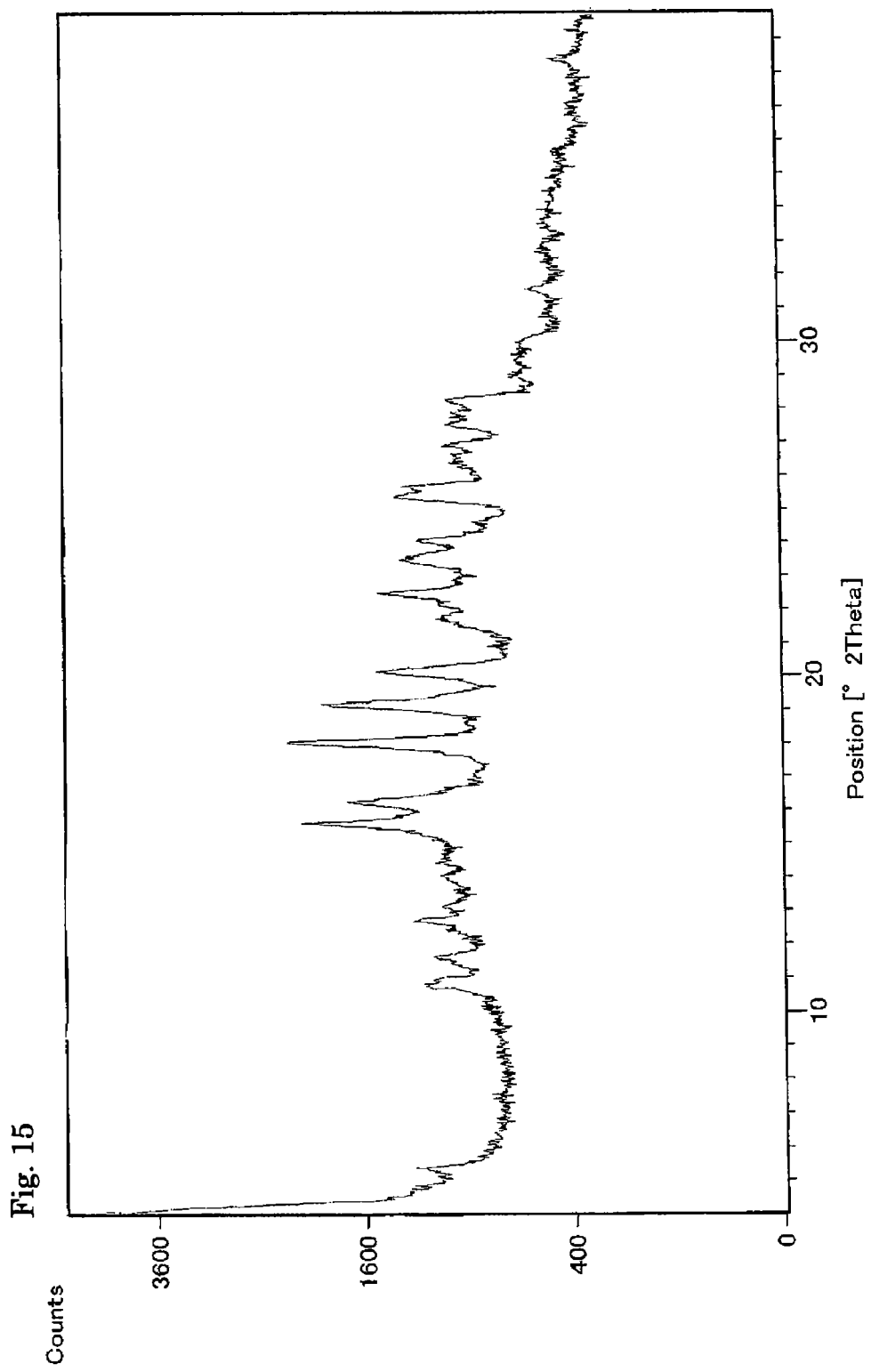
FIG. 15 is a diagram showing the powder X-ray diffraction pattern observed for the form S2 crystal according to the present invention wherein the angle of diffraction: 2 θ (degrees) is plotted as abscissa, while the intensity (counts) is plotted as ordinate.

Powder X-Ray Diffraction Pattern: FIG. 15

$^1$H-NMR (DMSO-d$_6$): δ 2.99-3.25 (dd, 2H), 3.10 (s, 6H), 3.52 (s, 3H), 3.69 (s, 3H), 4.79-4.85 (m, 1H), 6.10-7.80 (b, 2H), 7.19 (d, 2H), 7.38-7.47 (m, 5H), 7.54 (d, 1H), 7.71 (b, 2H), 9.27 (d, 1H)

Mass (ESI, Found Value): [M+H]$^+$ 568.9

Example 16

Production of Form S3 Crystal

The compound (I) (500 mg) in its free state was suspended in 1 mL of methanol, then 50 µL of sulfuric acid was added to the suspension and the mixture was stirred at room temperature for the dissolution of the compound (I). Thereafter, the resulting solution was dropwise added to 10 mL of methyl acetate to thus precipitate crystals. The crystals thus precipitated out of the mixture were separated and then dried at 60° C. under reduced pressure to thus give the title crystals (form S3 crystals) of sulfate of the compound (I).

Figure 16:
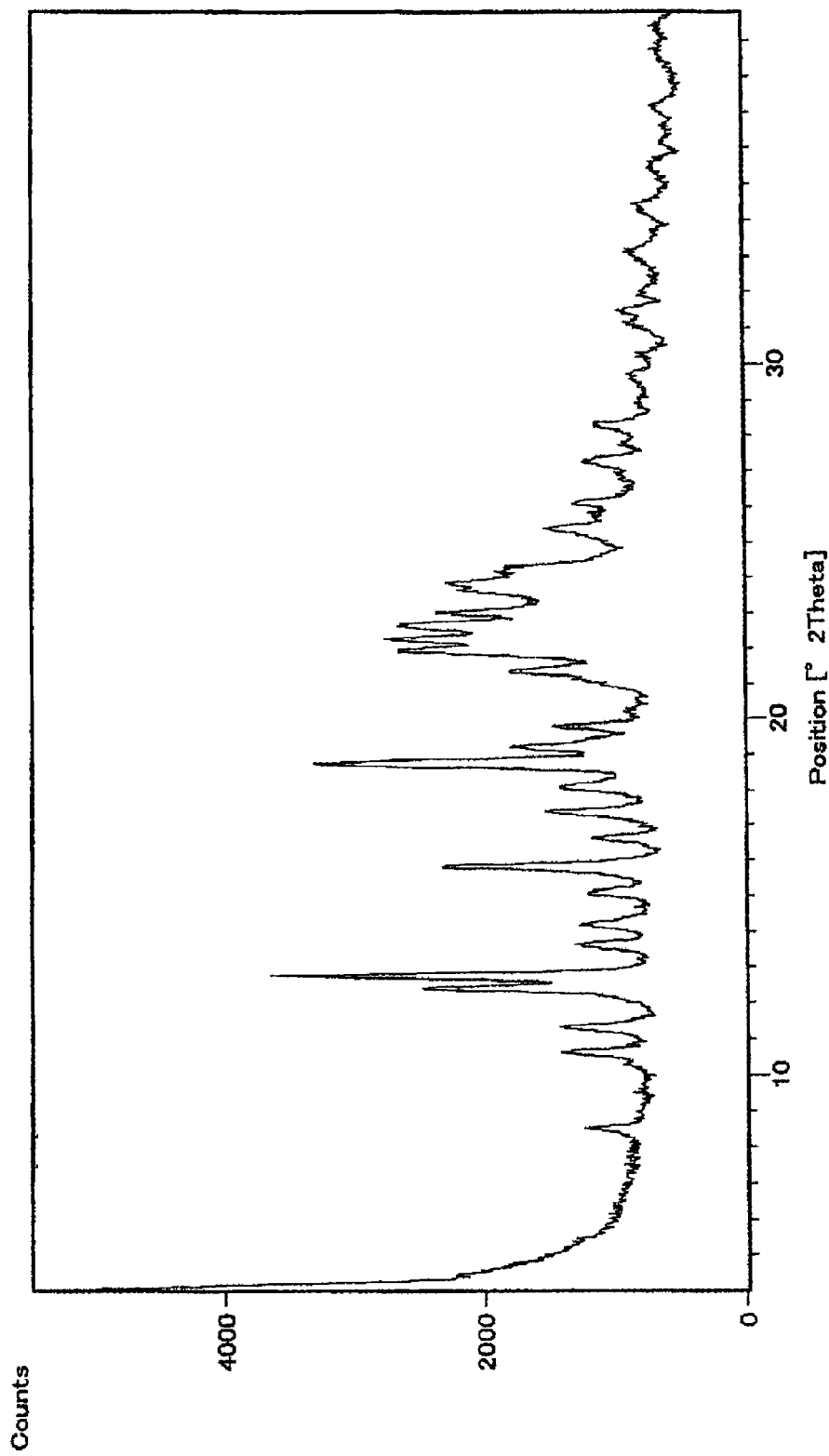
FIG. 16 is a diagram showing the powder X-ray diffraction pattern observed for the form S3 crystal according to the present invention wherein the angle of diffraction: 2 θ (degrees) is plotted as abscissa, while the intensity (counts) is plotted as ordinate.

Powder X-Ray Diffraction Pattern: FIG. 16

$^1$H-NMR (DMSO-d$_6$): δ 2.99-3.25 (dd, 2H), 3.12 (s, 6H), 3.53 (s, 3H), 3.69 (s, 3H), 4.79-4.85 (m, 1H), 7.19 (d, 2H), 7.38-7.47 (m, 5H), 7.58 (d, 1H), 7.80 (b, 2H), 9.27 (d, 1H), 9.40-10.1 (b, 2H)

Mass (ESI, Found Value): [M+H]$^+$ 569.3

Example 17

Production of Form S4 Crystal

There were added, in 8 mL of tetrahydrofuran, 500 mg of the sulfate crystals of the compound (I) and the resulting mixture was then stirred at room temperature to give a suspension. After the suspended material was removed, it was dried at 40° C. under reduced pressure to thus obtain 439.6 mg of the title sulfate crystals (form S4 crystals) of the compound (I) as a white solid.

Figure 17:
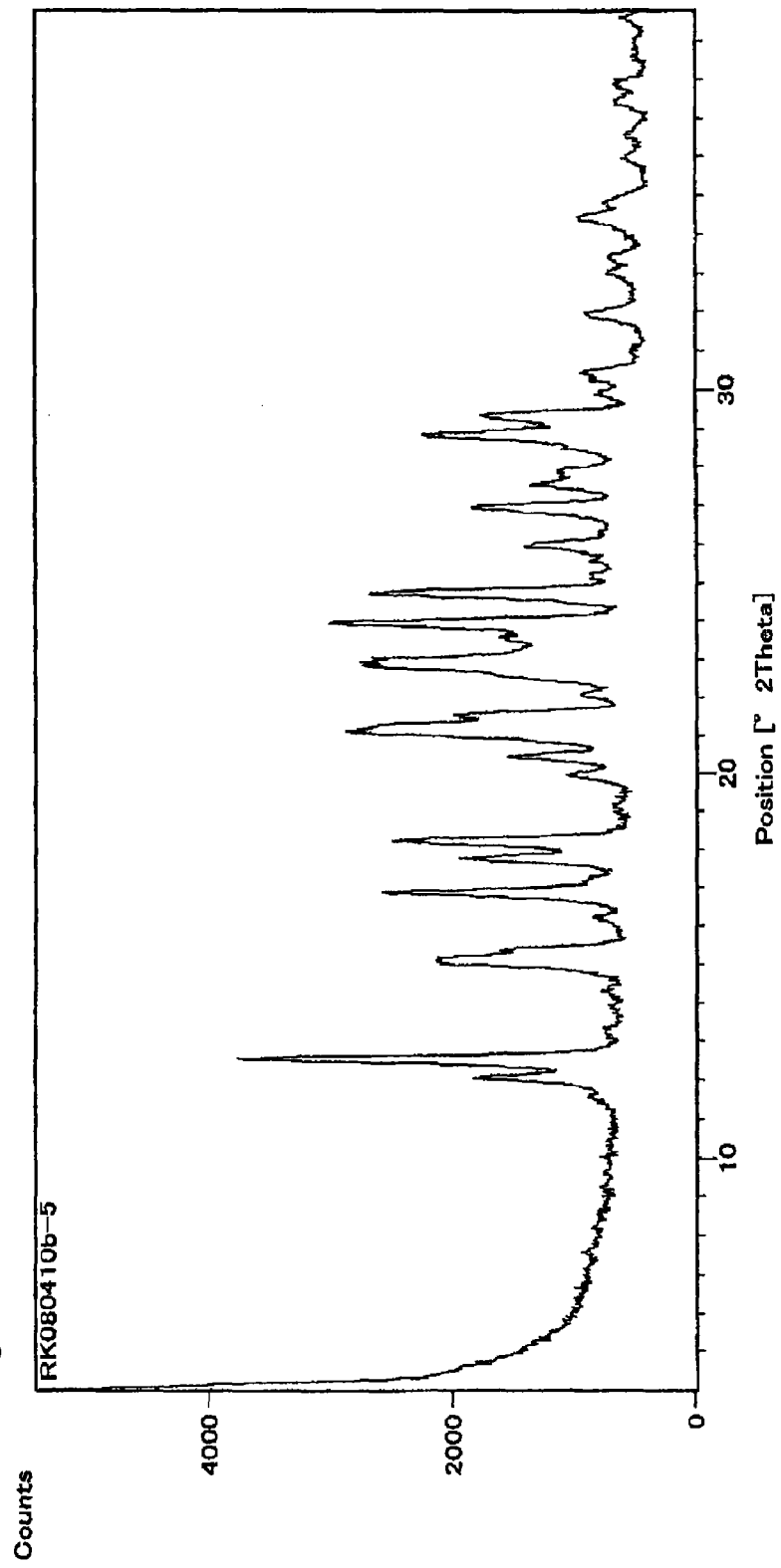
FIG. 17 is a diagram showing the powder X-ray diffraction pattern observed for the form S4 crystal according to the present invention wherein the angle of diffraction: 2 θ (degrees) is plotted as abscissa, while the intensity (counts) is plotted as ordinate.

Powder X-Ray Diffraction Pattern: FIG. 17

$^1$H-NMR (DMSO-d$_6$): δ 2.99-3.25 (dd, 2H), 3.06 (s, 6H), 3.52 (s, 3H), 3.69 (s, 3H), 4.78-4.84 (m, 1H), 7.19 (d, 2H), 7.39-7.46 (m, 5H), 7.48 (d, 1H), 7.55 (b, 2H), 9.27 (d, 1H)

Mass (ESI, Found Value): [M+H]$^+$ 568.9

IC (Determined as SO$_4$ Anion, Found Value): 23.5 w/w % (as H$_2$SO$_4$)

Example 18

Production of Form S5 Crystal

There were added, to 8 mL of tetrahydrofuran, 500 mg of the sulfate crystals of the compound (I) and the mixture was stirred at room temperature to form a suspension. The suspended material was separated from the suspension and then dried at 40° C. under reduced pressure to thus give 439.6 mg of the title sulfate crystals (form S5 crystals) of the compound (I) as a white solid.

Figure 18:
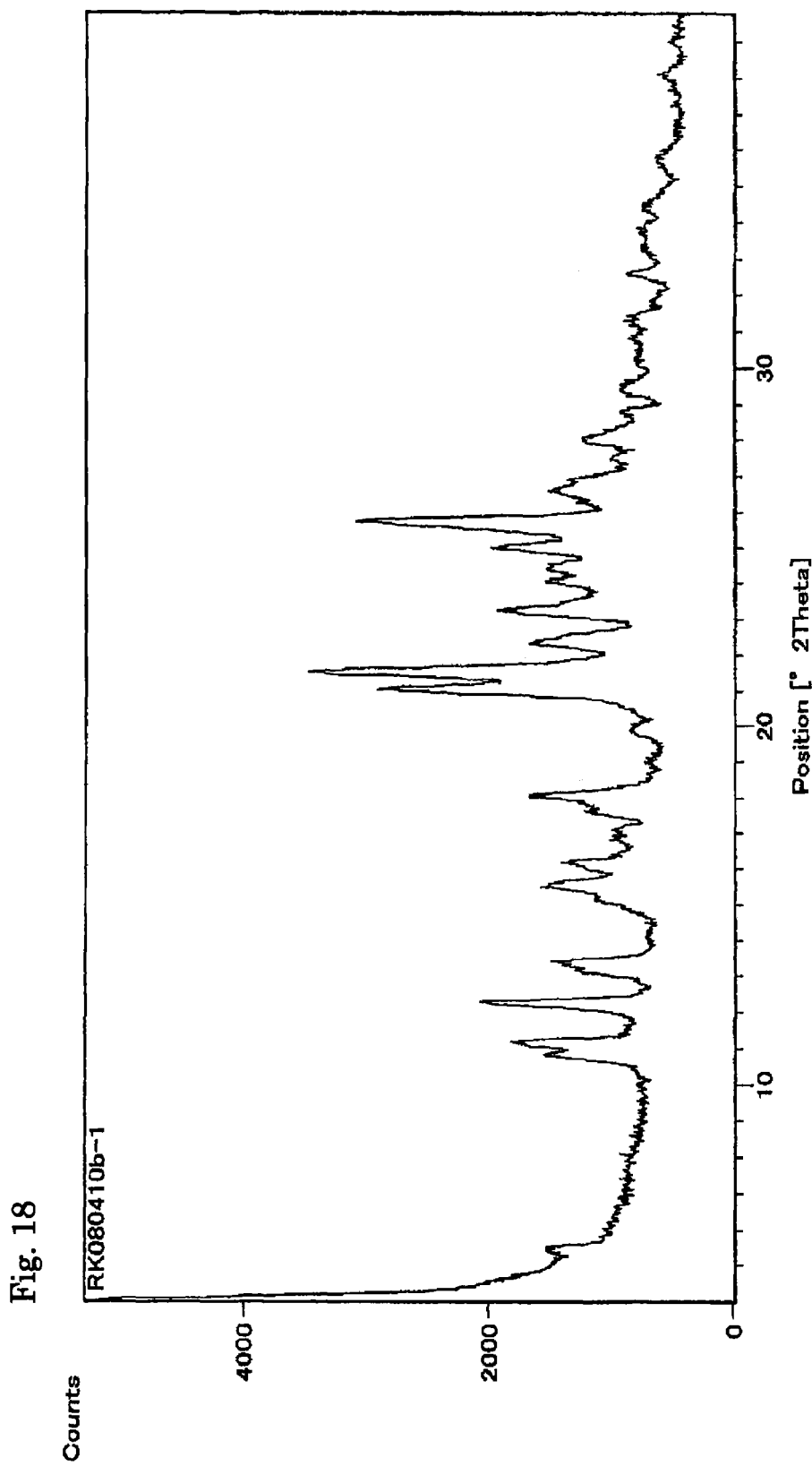
FIG. 18 is a diagram showing the powder X-ray diffraction pattern observed for the form S5 crystal according to the present invention wherein the angle of diffraction: 2 θ (degrees) is plotted as abscissa, while the intensity (counts) is plotted as ordinate.

Powder X-Ray Diffraction Pattern: FIG. 18

$^1$H-NMR (DMSO-d$_6$): δ 2.99-3.25 (dd, 2H), 3.06 (s, 6H), 3.52 (s, 3H), 3.69 (s, 3H), 4.78-4.84 (m, 1H), 5.86 (b, 5H), 7.19 (d, 2H), 7.38-7.47 (m, 5H), 7.51 (d, 1H), 7.60 (b, 2H), 9.27 (d, 1H)

Mass (ESI, Found Value): [M+H]$^+$ 568.9

IC (Determined as SO$_4$ Anion, Found Value): 21.0 w/w % (as H$_2$SO$_4$)

Example 19

Production of Form N1 Crystal

The compound (I) (500 mg) in its free state was suspended in 1 mL of methanol, then 80 μL of nitric acid was added to the suspension and the mixture was stirred at room temperature. Thereafter, the resulting mixed liquid was dropwise added to 5 mL of ethyl alcohol and the crystals thus precipitated out of the liquid were removed. The crystals were then dried under reduced pressure to thus give 442 mg of the title nitrate crystals (form N1 crystals) of the compound (I) as a white solid.

Figure 19:
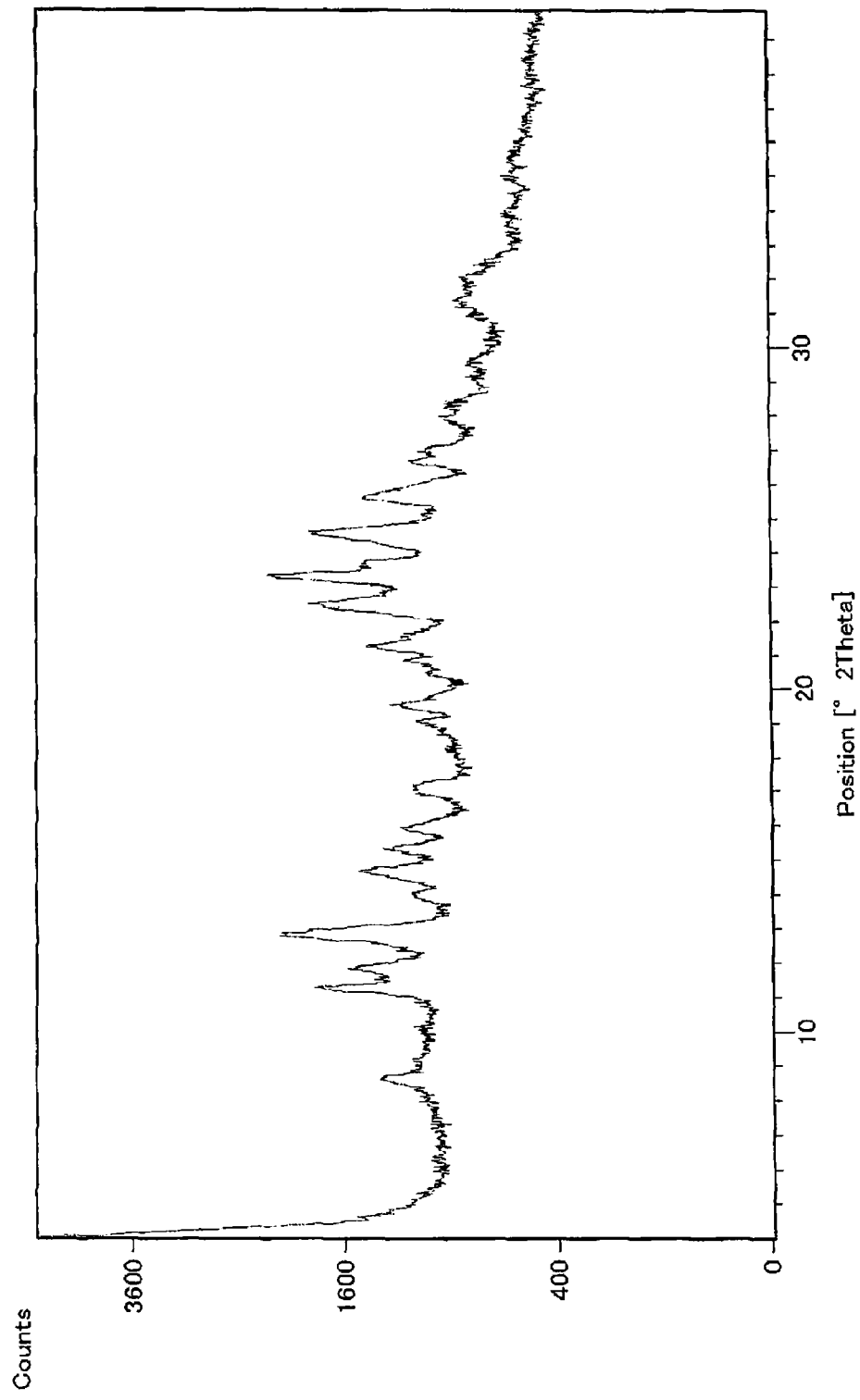
FIG. 19 is a diagram showing the powder X-ray diffraction pattern observed for the form N1 crystal according to the present invention wherein the angle of diffraction: 2 θ (degrees) is plotted as abscissa, while the intensity (counts) is plotted as ordinate.

Powder X-Ray Diffraction Pattern: FIG. 19

$^1$H-NMR (DMSO-d6): δ 2.99-3.25 (dd, 2H), 3.11 (s, 6H), 3.52 (s, 3H), 3.69 (s, 3H), 4.79-4.87 (m, 1H), 5.90-6.90 (b, 1H), 7.20 (d, 2H), 7.38-7.47 (m, 5H), 7.54 (d, 1H), 7.72 (b, 2H), 9.28 (d, 1H)

Mass (ESI, Found Value): [M+H]$^+$ 569.1

IC (Determined as NO$_3$ Anion, Found Value): 9.2 w/w % (as HNO$_3$)

Example 20

Production of Form N2 Crystal

There was suspended, in 1 mL of methanol, 500 mg of the compound (I) in its free state, then 86 μL of nitric acid was added to the suspension and the mixture was stirred at room temperature. Thereafter, the mixed liquid was dropwise added to 5 mL of isopropyl alcohol and the resulting crystals were separated from the mixture. Then the crystals were dried under reduced pressure to thus give 498 mg of the title nitrate crystals (form N2 crystals) of the compound (I) as a pale pink-colored solid.

Figure 20:
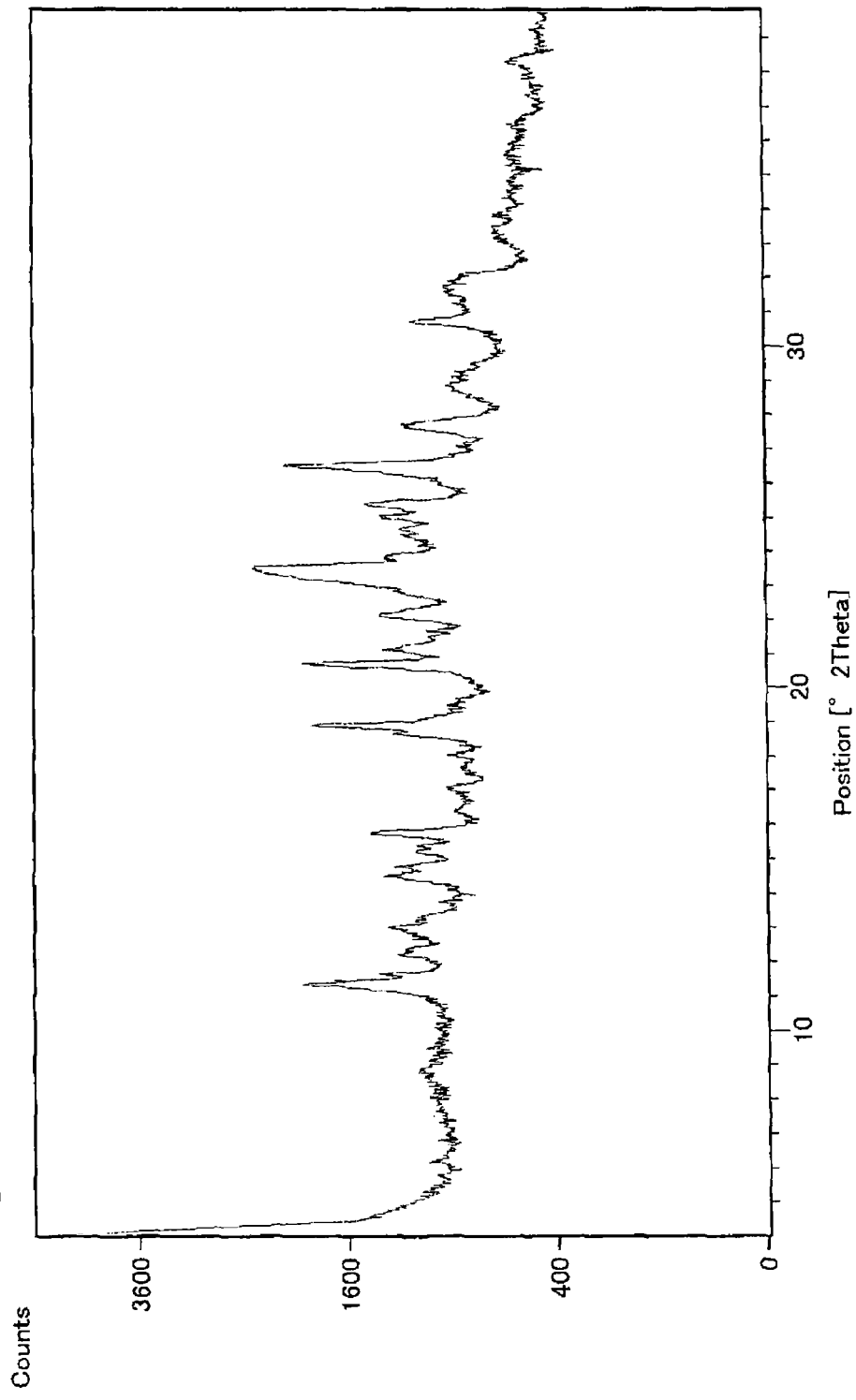
FIG. 20 is a diagram showing the powder X-ray diffraction pattern observed for the form N2 crystal according to the present invention wherein the angle of diffraction: 2 θ (degrees) is plotted as abscissa, while the intensity (counts) is plotted as ordinate.

Powder X-Ray Diffraction Pattern: FIG. 20

$^1$H-NMR (DMSO-d6): δ 2.99-3.28 (dd, 2H), 3.11 (s, 6H), 3.52 (s, 3H), 3.69 (s, 3H), 4.79-4.87 (m, 1H), 7.20 (d, 2H), 7.38-7.47 (m, 5H), 7.55 (d, 1H), 7.72 (b, 2H), 7.80-8.80 (b, 1H), 9.28 (d, 1H)

Mass (ESI, Found Value): [M+H]$^+$ 568.9

IC (Determined as NO$_3$ Anion, Found Value): 8.6 w/w % (as HNO$_3$)

Example 21

Production of Form Ts1 Crystal

There was suspended, in 0.5 mL of methanol, 500 mg of the compound (I) in its free state, then 182 mg of p-toluene-sulfonic acid monohydrate was added to the resulting suspension and the resulting mixture was stirred at room temperature. Subsequently, the resulting mixed liquid was dropwise added to 5 mL of ethyl alcohol, the crystals thus precipitated out of the mixed liquid were separated from the mixed liquid and then dried under reduced pressure to give 471 mg of the title p-toluene-sulfonate crystals (form Ts1 crystals) of the compound (I) as a white solid.

Figure 21:
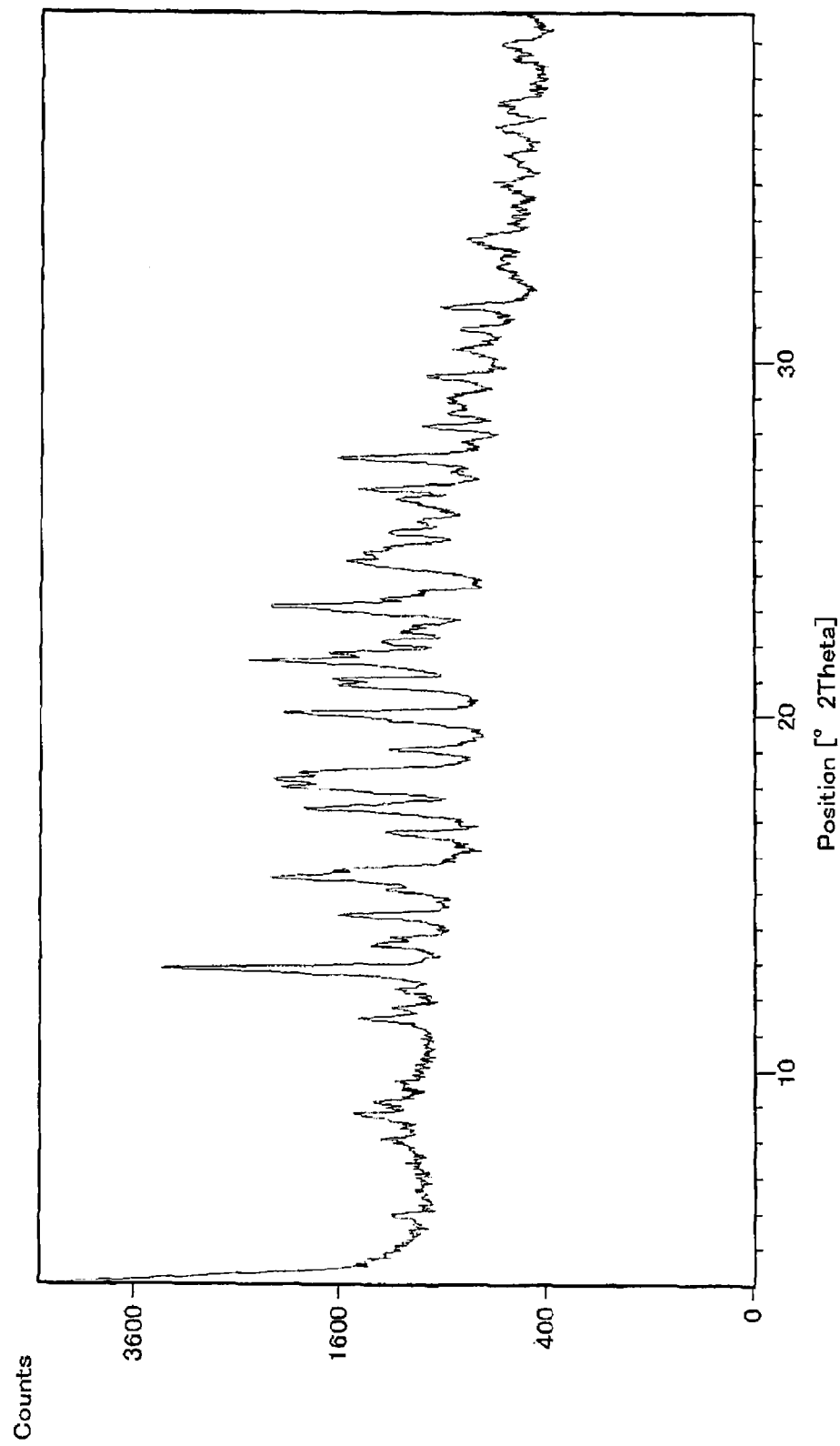
FIG. 21 is a diagram showing the powder X-ray diffraction pattern observed for the form Ts1 crystal according to the present invention wherein the angle of diffraction: 2 θ (degrees) is plotted as abscissa, while the intensity (counts) is plotted as ordinate.

Powder X-Ray Diffraction Pattern: FIG. 21

1H-NMR (DMSO-d6): δ 2.91 (s, 3H), 2.99-3.28 (dd, 2H), 3.11 (s, 6H), 3.52 (s, 3H), 3.69 (s, 3H), 4.79-4.87 (m, 1H), 7.12 (d, 2H), 7.20 (2H), 7.34 (d, 2H), 7.38-7.47 (m, 5H), 7.54 (d, 1H), 7.72 (b, 2H), 9.27 (d, 1H)

Mass (ESI, Found Value): [M+H]$^+$ 569.1

IC (Determined as Toluene-sulfonate Anion, Found Value): 22.9 w/w % (as TsOH)

Example 22

Production of Form Ms1 Crystal

There was suspended, in 1 mL of methanol, 500 mg of the compound (I) in its free state, then 60 μL of methane-sulfonic acid was added to the resulting suspension and the mixture was stirred at room temperature for the dissolution of the compound (I). This solution was dropwise added to 5 mL of ethyl alcohol and the mixture was stirred at room temperature. The solution was allowed to stand in a refrigerator to precipitate crystals and then the latter were separated through filtration. Then the crystals were dried at 50° C. under reduced pressure to thus give 466 mg of the title methane-sulfonate crystals (form Ms1 crystals) of the compound (I).

Figure 22:
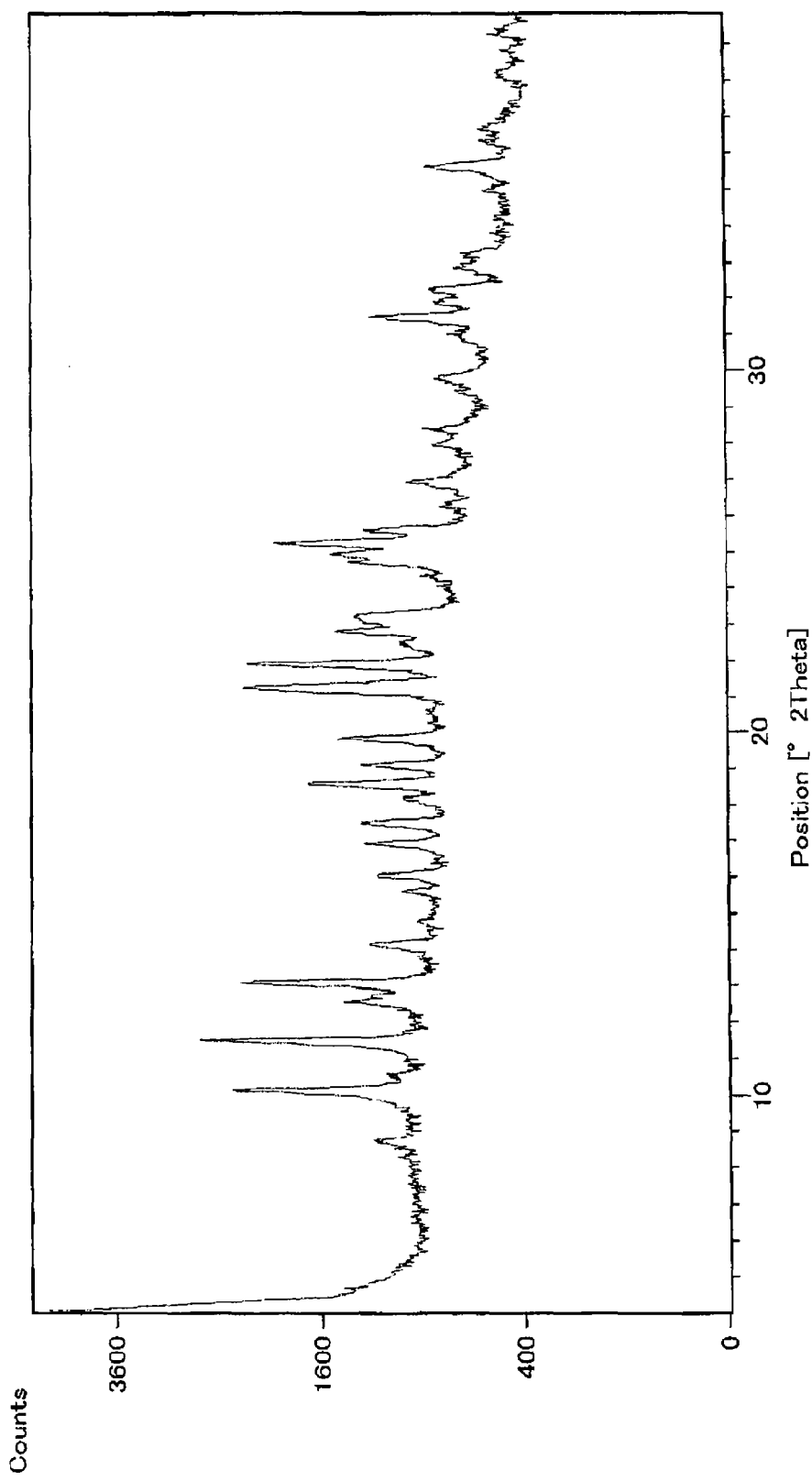
FIG. 22 is a diagram showing the powder X-ray diffraction pattern observed for the form Ms1 crystal according to the present invention wherein the angle of diffraction: 2 θ (degrees) is plotted as abscissa, while the intensity (counts) is plotted as ordinate.

Powder X-Ray Diffraction Pattern: FIG. 22

$^1$H-NMR (DMSO-d6): δ 2.42 (s, 3H), 2.99-3.28 (dd, 2H), 3.10 (s, 6H), 3.52 (s, 3H), 3.69 (s, 3H), 4.79-4.87 (m, 1H), 7.19 (d, 2H), 7.38-7.47 (m, 5H), 7.54 (d, 1H), 7.72 (b, 2H), 9.28 (d, 1H)

Mass (ESI, Found Value): [M+H]+569.1

IC (Determined as Methane-sulfonate Anion, Found Value): 13.3 w/w % (as MsOH)

Example 23

Production of Form Ms2 Crystal

There was suspended, in 10 mL of methanol, 5.0 g of the compound (I) in its free state, then 600 μL of methane-sulfonic acid was added to the resulting suspension and the mixture was stirred at room temperature for the dissolution of the compound (I). This solution was dropwise added to 50 mL of isopropyl alcohol (IPA, 2-propanol), then the mixture was stirred at room temperature for a period of time for the initiation of the crystallization and thereafter the mixture was allowed to stand overnight in a refrigerator. The crystals thus precipitated out of the mixture were separated from the mixture, washed with 20 mL of methyl acetate to give wet crystals and the latter was dried at 60° C. under reduced pressure to thus give 4.38 g of the title methane-sulfonate crystals (form Ms2 crystals) of the compound (I) as a white solid.

Figure 23:
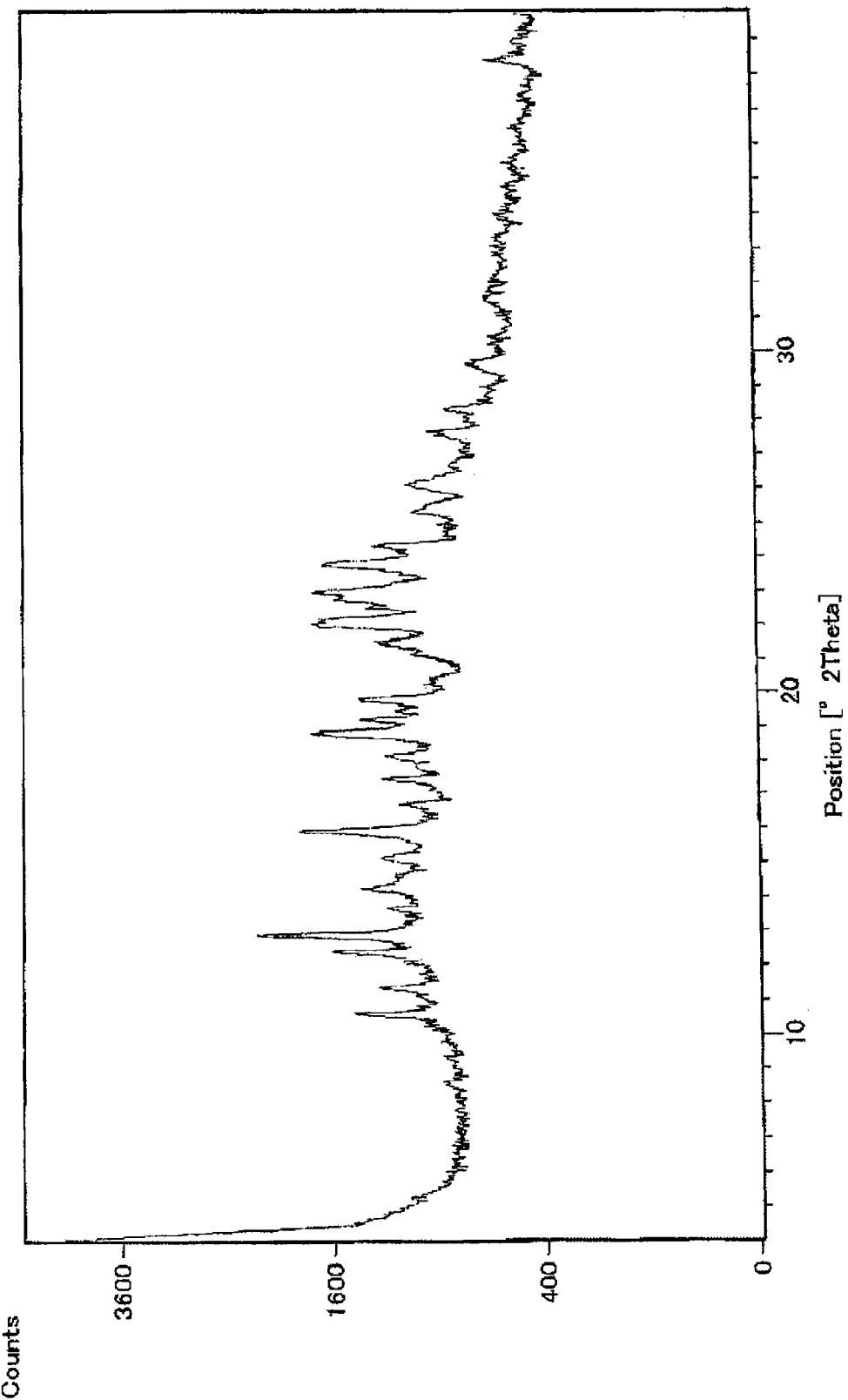
FIG. 23 is a diagram showing the powder X-ray diffraction pattern observed for the form Ms2 crystal according to the present invention wherein the angle of diffraction: 2 θ (degrees) is plotted as abscissa, while the intensity (counts) is plotted as ordinate.

Powder X-Ray Diffraction Pattern: FIG. 23

$^1$H-NMR (DMSO-d6): δ 2.40 (s, 3H), 2.99-3.25 (dd, 2H), 3.09 (s, 6H), 3.52 (s, 3H), 3.69 (s, 3H), 4.79-4.85 (m, 1H), 7.19 (d, 2H), 7.38-7.47 (m, 5H), 7.53 (d, 1H), 7.68 (b, 2H), 9.27 (d, 1H)

Mass (ESI, Found Value): [M+H]+ 569.1

IC (Determined as Methane-sulfonate Anion, Found Value): 14.2 w/w % (as MsOH)

Example 24

Production of Form Ms3 Crystal

There was suspended, in 10 mL of methanol, 5 g of the compound (I) in its free state, then 600 μL of methane-sulfonic acid was added to the resulting suspension and the mixture was stirred at room temperature for the dissolution of the compound (I). The resulting solution was dropwise added to 50 mL of ethyl alcohol, the crystals precipitated out of the resulting mixture were separated from the solution and then they were washed with ethyl alcohol to give wet crystals. The resulting wet crystals were dried at 50° C. under reduced pressure to give 5.70 g of the title methane-sulfonate crystals (form Ms3 crystals) of the compound (I).

Figure 24:
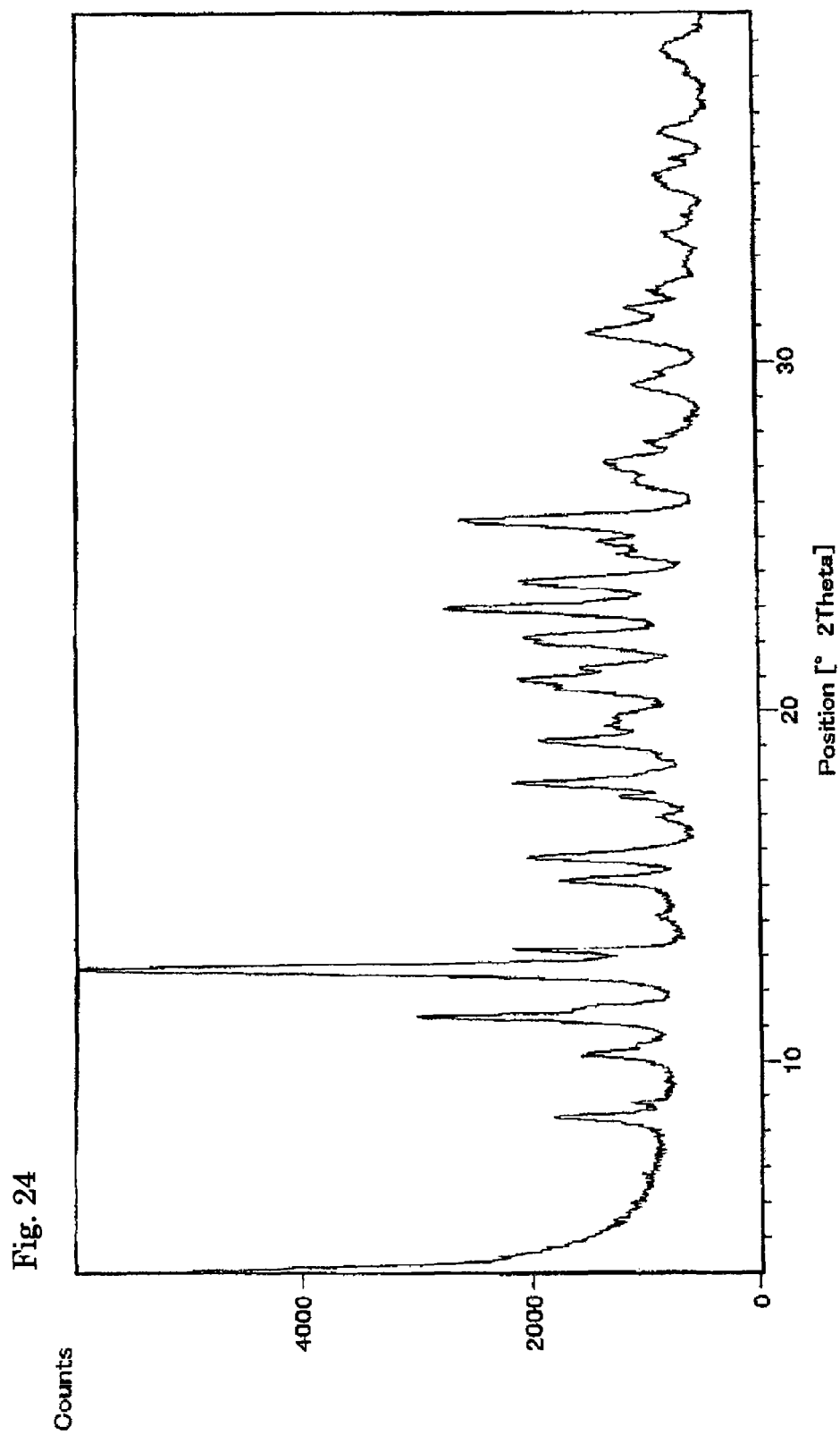
FIG. 24 is a diagram showing the powder X-ray diffraction pattern observed for the form Ms3 crystal according to the present invention wherein the angle of diffraction: 2 θ (degrees) is plotted as abscissa, while the intensity (counts) is plotted as ordinate.

Powder X-Ray Diffraction Pattern: FIG. 24

$^1$H-NMR (DMSO-d$_6$): δ 2.42 (s, 3H), 2.99-3.25 (dd, 2H), 3.11 (s, 6H), 3.53 (s, 3H), 3.69 (s, 3H), 4.79-4.87 (m, 1H), 7.19 (d, 2H), 7.38-7.47 (m, 5H), 7.55 (d, 1H), 7.78 (b, 2H), 9.28 (d, 1H)

Mass (ESI, Found Value): [M+H]$^+$ 568.9

IC (Determined as Methane-sulfonate Anion, Found Value): 14.3 w/w % (as MsOH)

Example 25

Production of Form Ms4 Crystal

There was suspended, in 3 mL of methanol, 10 g of the compound (I) in its free state, then 1.2 mL of methane-sulfonic acid was added to the resulting suspension and the mixture was stirred at room temperature to give a suspension. After the dropwise addition of the suspension to 40 mL of acetone, the mixture was stirred at 50° C. for the dissolution of the compound (I), the resulting solution was cooled down to 10° C. and the crystals thus precipitated out of the solution were separated from the solution to thus obtain wet crystals. The resulting wet crystals were dried at 40° C. under reduced pressure to give 11.1 g of the title methane-sulfonate crystals (form Ms4 crystals) of the compound (I).

Figure 25:
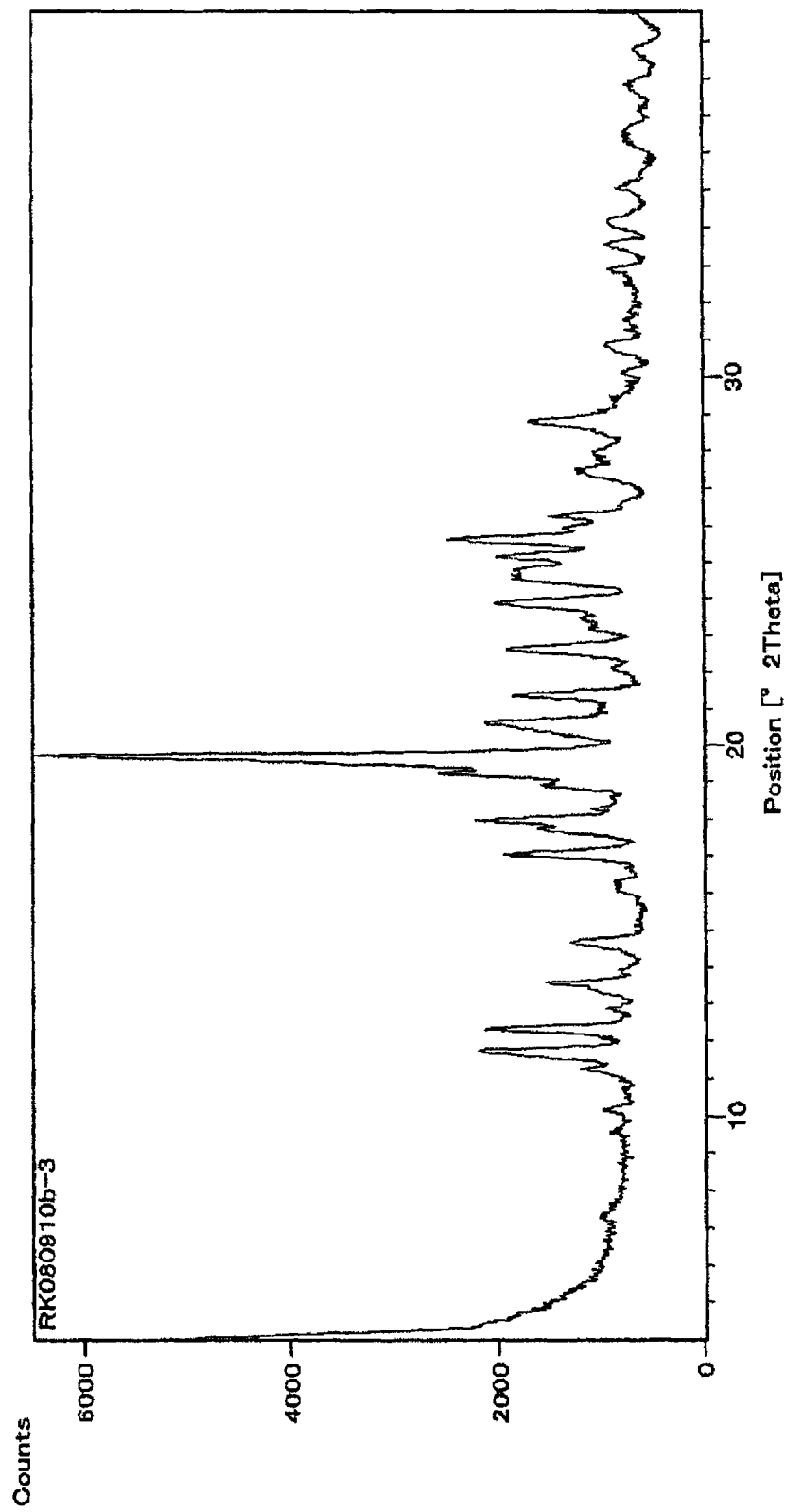
FIG. 25 is a diagram showing the powder X-ray diffraction pattern observed for the form Ms4 crystal according to the present invention wherein the angle of diffraction: 2 θ (degrees) is plotted as abscissa, while the intensity (counts) is plotted as ordinate.

Powder X-Ray Diffraction Pattern: FIG. 25

$^1$H-NMR (DMSO-d$_6$) δ 2.42 (s, 3H), 2.99-3.25 (dd, 2H), 3.11 (s, 6H), 3.53 (s, 3H), 3.69 (s, 3H), 4.79-4.87 (m, 1H), 7.19 (d, 2H), 7.38-7.47 (m, 5H), 7.55 (d, 1H), 7.78 (b, 2H), 9.28 (d, 1H)

Mass (ESI, Found Value): [M+H]$^+$ 568.9

IC (Determined as Methane-sulfonate Anion, Found Value): 14.3 w/w % (as MsOH)

Determination Method 1: Powder X-Ray Diffraction Pattern

The following are the conditions for the determination of the powder X-ray diffraction patterns disclosed in the foregoing Examples 1 to 25:

Device Used: X'Pert (available from PANalytical B.V.);
Target Used: Cu Full-Automatic Monochromater;
Established Output of X-Ray: 401V, 30 mA;
Divergence Slit: Type: Fixed type one, Size: 1.0000°
Slit: Divergence: ½°
:Scattering: ½°
:Light Receipt: 0.15 mm
Scan Speed: 2°/min
2 θ Range: 4 to 40°

Determination Method 2: Nuclear Magnetic Resonance (NMR) Spectroscopy

The NMR spectral data disclosed in the foregoing Examples 1 to 13 were determined using Bruker Avance 400 NMR Spectrometer, while using, as standards, TMS (δ 0.00) for the $^1$H-NMR spectral data and DMSO-d$_6$ (δ 39.7) for the $^{13}$C-NMR spectral data. The solvent used for the determination was DMSO-d6 contained in an ampoule (0.75 mL) available from Eurisotop Company, unless otherwise specified.

Determination Method 3: Ion-Chromatography (IC)

Each IC value disclosed in the foregoing Examples is expressed in terms of the concentration by mass of the corresponding acid component in the crystal estimated on the basis of the amount of anions determined according to the following method and it is determined on the basis of the results obtained in the following ion-chromatography measurement. The compound represented by the foregoing formula (I) was suspended in deionized water, the suspension was passed through a disposable filter overnight and then each ion-chromatography datum was determined under the following conditions. In this connection, however, used herein as reference liquid were those obtained by diluting KCl, KBr, K$_2$SO$_4$, TsOH, MsOH or HNO$_3$ with deionized water.

(Conditions for Ion-Chromatography)

Device Used: Ion-Chromatograph DX-120 (available from DIONEX Company);

Eluting Solution: 1.0 M Na$_2$CO$_3$/1.0 M NaHCO$_3$/Deionized water=2.7/0.3/997

Test Example 1

Determination of Solubility

After 50 mg each of samples of the crystals prepared according to the foregoing methods and the crystal of the compound (I) in its free state was suspended in 10 mL of distilled water and then each suspension was stirred at room temperature for 15 minutes, the supernatant of each suspension was collected, then passed through a disposable filter of 0.2 μm for HPLC, 1 to 3.5 g of each filtered supernatant was dispensed, the volume thereof was increased up to 10 mL with a 90% aqueous solution of acetonitrile and finally the content of the compound (I) present in the supernatant was determined according to the HPLC while using the following conditions. The results thus obtained are summarized in the following Table 1.

(Conditions for the HPLC Analysis)

Device Used: LC-10A Series (available from Shimadzu Corporation);
Column: Inertsil (available from GL Science Company) ODS-24.5 mm×150 mm, 5 μm, 40° C.;
Flow Rate: 1 mL/min, UV at 254 nm, 10 μL Injection;
Eluting Solution A: 0.1% TFA (trifluoroacetic acid)/water;
Eluting Solution B: 0.1% TFA/MeCN;
Gradient Program: 0→25 min (B: 0→90%).

TABLE 1

| Entry | Form of Salt (Crystalline Form) | Solubility in Water (25° C., μg/mL, 15 min) |
|---|---|---|
| Control | Free State | 0.12 |
| 1 | Hydrochloride (Form Cl1) | 122 |
| 2 | Hydrochloride (Form Cl2) | 101 |
| 3 | Hydrochloride (Form Cl3) | 102 |
| 4 | Hydrochloride (Form Cl5) | 91 |
| 5 | HBr salt (Form Br1) | 120 |
| 6 | HBr salt (Form Br2) | 123 |
| 7 | Sulfate (Form S1) | 104 |
| 8 | Sulfate (Form S2) | 129 |
| 9 | Sulfate (Form S3) | 119 |
| 10 | Nitrate (Form N1) | 110 |
| 11 | Nitrate (Form N2) | 128 |
| 12 | Toluene-sulfonate (Form Ts1) | 97 |
| 13 | Methane-sulfonate (Form Ms1) | 102 |
| 14 | Methane-sulfonate (Form Ms2) | 115 |
| 15 | Methane-sulfonate (Form Ms3) | 109 |
| 16 | Methane-sulfonate (Form Ms4) | 94 |

Thus, the data listed in the foregoing Table 1 clearly indicate that all of the crystals of the compound (I) with pharmaceutically acceptable acids, according to the present invention are considerably improved in their solubility in water as compared with that observed for the crystal of the compound (I) in its free state and that they are substantially valuable for use as pharmaceutical agents.

Test Example 2

Determination of Storage Stability

The crystal of a salt of the compound represented by the formula (I) was inspected for the storage stability, when it was stored at 40° C., 75% RH over two months, according to the following method. The results observed for preferred crystals, i.e., forms Cl1, Br1, Br2, Ms1 and Ms3 crystals, among others, are summarized in the following Table 2. The data listed in Table 2 indicate that the crystals of the compound (I) in their preferred crystalline forms according to the present invention are particularly excellent in their storage stability.

Method for Determination:

The storage stability of each sample, which had been stored in a depository at 40° C., 75% RH over two months, was determined according to the HPLC analysis method.

More specifically, about 25 mg each of the crystals of the compound represented by the formula (I) was dispensed into a 50 mL volume measuring flask and then dissolved in a 90% aqueous solution of acetonitrile containing 0.1% TFA and the storage stability of the resulting solution was determined by the HPLC analysis under the following conditions.

(Conditions for HPLC Analysis)

Device Used: LC-10A Series (available from Shimadzu Corporation);

Column: Inertsil (available from GL Science Company) ODS-2 4.5 mm×150 mm, 5 μm, 40° C.;

Flow Rate: 1 mL/min, UV at 254 nm, 10 μL Injection;

Eluting Solution A: 0.1% TFA (trifluoroacetic acid)/water;

Eluting Solution B: 0.1% TFA/MeCN;

Gradient Program: 0→25 min (B: 0→90%).

TABLE 2

| Crystalline Form, PXRD | Accelerated Test, Stability, 40° C., 75% RH 2M |
|---|---|
| Form Cl1 | 99.03% of the initial sample was still in existence. |
| Form Br1 | 99.05% of the initial sample was still in existence. |
| Form Br2 | 98.13% of the initial sample was still in existence and 1.17% thereof was converted into the hydrolyzates. |
| Form Ms1 | 99.06% of the initial sample was still in existence. |
| Form Ms3 | 97.41% of the initial sample was still in existence and 1.81% thereof was converted into the hydrolyzates. |

Test Example 3

Determination of Adsorption-Desorption of Water Vapor

The crystals of the present invention were inspected for their water vapor adsorption-desorption ability using BELLSORP-aqua3 available from Nippon Bell Co., Ltd. More specifically, about 300 mg of the compound represented by the formula (I) was dispensed into a measuring tube, dried at 50° C. for 30 minutes and the amount of water vapor adsorbed on or desorbed from the crystal was determined under the following conditions:

Adsorption Temperature: 25° C.; Equilibration Time: 500 sec; Saturated Vapor Pressure: 3.169 kPa;

Excessively Introduced Amount: 0.2 or 1.0 cm$^3$ (STP)/g; Tolerance for Increase or Decrease of Adsorbed Amount: 0.2 or 1.0 cm$^3$ (STP)/g.

Figure 26:
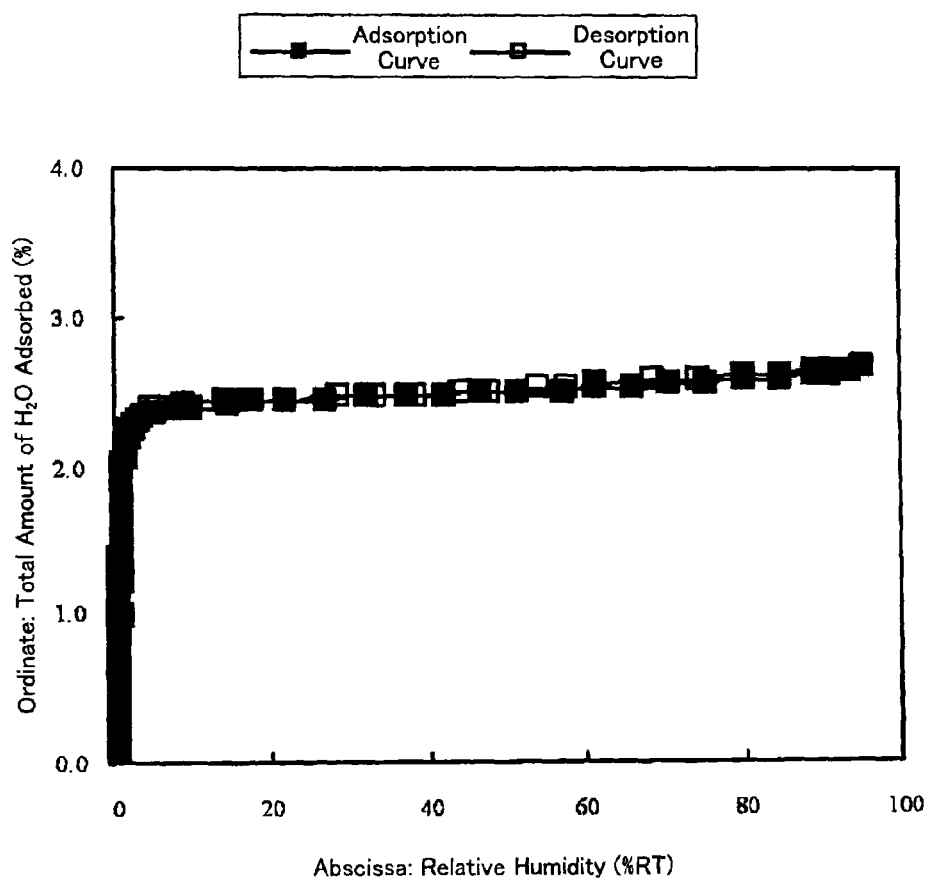
FIG. 26 is a diagram showing the isothermal vapor absorption-desorption curve observed for the form Cl 1 crystal according to the present invention.
Figure 27:
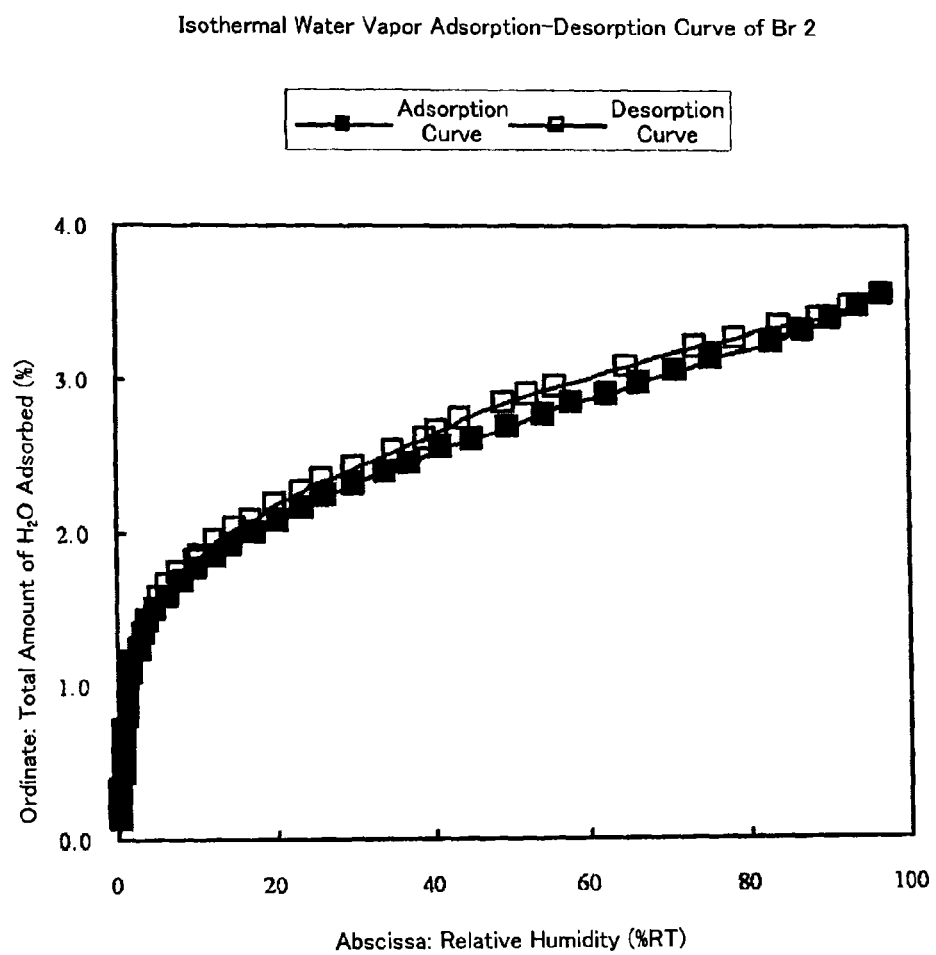
FIG. 27 is a diagram showing the isothermal vapor absorption-desorption curve observed for the form Br2 crystal according to the present invention.
Figure 28:
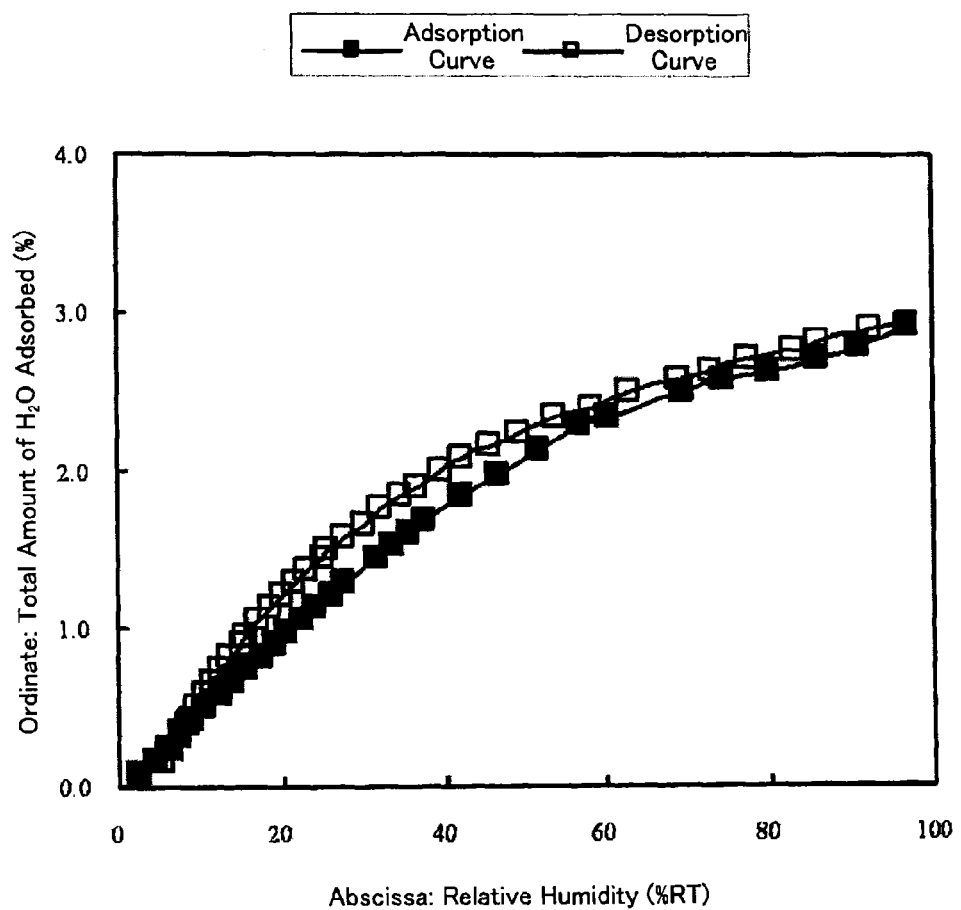
FIG. 28 is a diagram showing the isothermal vapor absorption-desorption curve observed for the form Ms1 crystal according to the present invention.

FIGS. 26, 27 and 28 show the isothermal water vapor adsorption-desorption curves observed for the resulting form Cl1 crystal, form Br2 crystal and form Ms1 crystal according to the present invention, respectively. In all the figures, it was found that the amount of adsorbed water is on a level of less than 3.0% to 4.0% and that any crystal undergoes only a very slight change in its crystalline state even at a high humidity. Accordingly, it was clearly confirmed that these salts are quite stable and that they show preferred crystalline characteristics.

INDUSTRIAL APPLICABILITY

The crystals of salts of the compound (I) according to the present invention, which are useful as a 4-integrin-inhibitory agents, can easily be handled, are excellent in the solubility in water, and are useful as effective components of therapeutic agents or prophylactic agents for treating or preventing inflammatory diseases, in which the α 4-integrin-dependent adhesion process is involved in the pathema, rheumatoid arthritis, inflammatory intestinal diseases, systemic lupus erythematosus, disseminated or multiple sclerosis, Sjogren's syndrome, asthma, psoriasis, allergy, diabetes (mellitus), cardiovascular diseases, arterial sclerosis, restenosis, tumor hyperplasia, tumor metastasis, and graft rejection.

What is claimed is:

1. A method of treating rheumatoid arthritis, inflammatory, intestinal diseases, systemic lupus erythematosus, disseminated or multiple sclerosis, Sjogren's syndromes, asthma, psoriasis, allergy, diabetes (mellitus), cardiovascular diseases, arterial sclerosis, restenosis, tumor hyperplasia, tumor metastasis, or graft rejection, comprising administering to a subject in need thereof an effective amount of a the compound represented by formula (I):

or a pharmaceutically-acceptable acid addition salt thereof, and

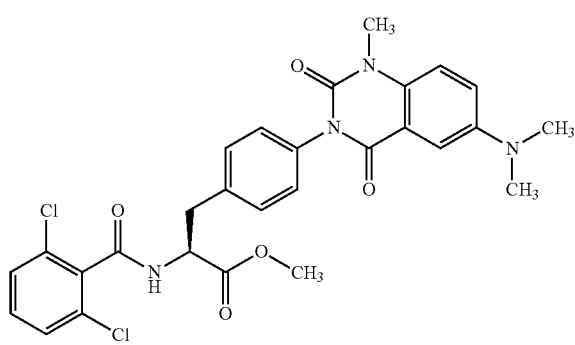

at least one additional pharmaceutical agent selected from the group consisting of 5-ASA pharmaceutical preparations, adrenocortical hormone-containing pharmaceutical preparations, antibacterial agents, immunosuppressive agents and anti-cytokine agents.

2. The method of claim 1, which is a method of treating an inflammatory intestinal disease.

3. The method of claim 1, which is a method of treating Crohn's disease.

4. The method of claim 1, which is a method of treating ulcerative colitis.

5. The method of claim 1, wherein the compound represented by formula (I) is in the form of a pharmaceutically-acceptable acid addition salt.

6. The method of claim 1, wherein the compound represented by formula (I) is in the form of a crystal of a pharmaceutically-acceptable acid addition salt.

7. The method of claim 1, wherein the compound represented by formula (I) is a hydrochloric acid addition salt.

8. The method of claim 1, wherein the compound represented by formula (I) is in the form of a crystal of a hydrochloric acid addition salt.

9. The method of claim 1, wherein the additional pharmaceutical agent is a 5-ASA pharmaceutical preparation which is mesalazine or salzosulfapyrizine.

10. The method of claim 1, wherein the additional pharmaceutical agent is a anti-cytokine agent selected from the group consisting of anti-TNF antibodies, anti-IL6-receptor antibodies, anti-IL-12/23 antibodies and anti-IL-17 receptor antibodies.

* * * * *